United States Patent
Kimchy et al.

(10) Patent No.: US 7,652,259 B2
(45) Date of Patent: Jan. 26, 2010

(54) APPARATUS AND METHODS FOR IMAGING AND ATTENUATION CORRECTION

(75) Inventors: Yoav Kimchy, Haifa (IL); Roni Amrami, Yokneam (IL); Yoel Zilberstein, Haifa (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 171 days.

(21) Appl. No.: 10/533,568

(22) PCT Filed: Nov. 4, 2003
(Under 37 CFR 1.47)

(86) PCT No.: PCT/IL03/00917

§ 371 (c)(1),
(2), (4) Date: Jan. 5, 2006

(87) PCT Pub. No.: WO2004/042546

PCT Pub. Date: May 21, 2004

(65) Prior Publication Data
US 2006/0237652 A1  Oct. 26, 2006

Related U.S. Application Data

(60) Provisional application No. 60/423,359, filed on Nov. 4, 2002.

(51) Int. Cl.
*G01T 1/24* (2006.01)
*A61B 5/05* (2006.01)

(52) U.S. Cl. .................. 250/370.08; 600/407; 600/424; 600/427; 600/442

(58) Field of Classification Search ............ 250/370.08; 600/407, 424, 427, 442
See application file for complete search history.

(56) References Cited

U.S. PATENT DOCUMENTS 2,776,377 A   1/1957 Anger
(Continued)

FOREIGN PATENT DOCUMENTS

DE   19814199   7/1999
(Continued)

OTHER PUBLICATIONS

Rajshekhar "Continuous Impedence Monitoring During CT-Guided Stereotactic Surgery: Relative Value in Cystic and Solid Lesions", British Journal of Neurosurgery, 6: 439-444, 1992.
(Continued)

*Primary Examiner*—David P Porta
*Assistant Examiner*—Jessica L Eley

(57) ABSTRACT

Imaging apparatus, is provided, comprising a first device, for obtaining a first image, by a first modality, selected from the group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof, and a second device, for obtaining a second, structural image, by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, an intravascular ultrasound, and a combination thereof, and wherein the apparatus further includes a computerized system, configured to construct an attenuation map, for the first image, based on the second, structural image. Additionally, the computerized system is configured to display an attenuation-corrected first image as well as a superposition of the attenuation-corrected first image and the second, structural image. Furthermore, the apparatus is operative to guide an in-vivo instrument based on the superposition.

32 Claims, 17 Drawing Sheets

U.S. PATENT DOCUMENTS

| | | | |
|---|---|---|---|
| 3,340,866 A | 9/1967 | Nöller | |
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 4,015,592 A | 4/1977 | Bradley-Moore | |
| 4,278,077 A | 7/1981 | Mizumoto | |
| 4,364,377 A | 12/1982 | Smith | |
| 4,521,688 A | 6/1985 | Yin | |
| H12 H | 1/1986 | Bennett et al. | |
| 4,595,014 A | 6/1986 | Barrett et al. | |
| 4,674,107 A | 6/1987 | Urban et al. | |
| 4,689,041 A | 8/1987 | Corday et al. | |
| 4,689,621 A | 8/1987 | Kleinberg | |
| 4,731,536 A | 3/1988 | Rische et al. | |
| 4,773,430 A | 9/1988 | Porath | |
| 4,828,841 A | 5/1989 | Porter et al. | |
| 4,844,067 A | 7/1989 | Ikada et al. | |
| 4,844,076 A | 7/1989 | Lesho et al. | |
| 4,893,013 A | 1/1990 | Denen et al. | |
| 4,928,250 A | 5/1990 | Greenberg et al. | |
| 4,929,832 A | 5/1990 | Ledley | |
| 4,951,653 A * | 8/1990 | Fry et al. | 601/3 |
| 4,959,547 A | 9/1990 | Carroll et al. | |
| 4,995,396 A | 2/1991 | Inaba et al. | |
| 5,014,708 A | 5/1991 | Hayashi et al. | |
| 5,032,729 A | 7/1991 | Charpak | |
| 5,033,998 A | 7/1991 | Corday et al. | |
| 5,070,878 A | 12/1991 | Denen | |
| 5,088,492 A | 2/1992 | Takayama et al. | |
| 5,119,818 A | 6/1992 | Carroll et al. | |
| 5,151,598 A | 9/1992 | Denen | |
| 5,170,055 A | 12/1992 | Carroll et al. | |
| 5,170,789 A | 12/1992 | Narayan et al. | |
| 5,243,988 A * | 9/1993 | Sieben et al. | 600/463 |
| 5,246,005 A | 9/1993 | Carroll et al. | |
| 5,249,124 A | 9/1993 | DeVito | |
| 5,279,607 A | 1/1994 | Schentag et al. | |
| 5,299,253 A | 3/1994 | Wessels | |
| 5,307,808 A | 5/1994 | Dumoulin et al. | |
| 5,349,190 A | 9/1994 | Hines et al. | |
| 5,383,456 A | 1/1995 | Arnold et al. | |
| 5,395,366 A | 3/1995 | D'Andrea et al. | |
| 5,399,868 A | 3/1995 | Jones et al. | |
| 5,415,181 A | 5/1995 | Hofgrefe et al. | |
| 5,441,050 A | 8/1995 | Thurston et al. | |
| 5,448,073 A | 9/1995 | Jeanguillaume | |
| 5,475,219 A | 12/1995 | Olson | |
| 5,484,384 A | 1/1996 | Fearnot | |
| 5,489,782 A | 2/1996 | Wernikoff | |
| 5,493,595 A | 2/1996 | Schoolman | |
| 5,519,221 A | 5/1996 | Weinberg | |
| 5,572,999 A * | 11/1996 | Funda et al. | 600/118 |
| 5,579,766 A | 12/1996 | Gray | |
| 5,604,531 A | 2/1997 | Iddan et al. | |
| 5,617,858 A | 4/1997 | Taverna et al. | |
| 5,635,717 A | 6/1997 | Popescu | |
| 5,657,759 A | 8/1997 | Essen-Moller | |
| 5,672,877 A * | 9/1997 | Liebig et al. | 250/363.04 |
| 5,682,888 A | 11/1997 | Olson et al. | |
| 5,690,691 A | 11/1997 | Chen et al. | |
| 5,694,933 A | 12/1997 | Madden et al. | |
| 5,716,595 A | 2/1998 | Goldenberg | |
| 5,727,554 A | 3/1998 | Kalend et al. | |
| 5,729,129 A | 3/1998 | Acker | |
| 5,732,704 A | 3/1998 | Thurston et al. | |
| 5,744,805 A | 4/1998 | Raylman et al. | |
| 5,784,432 A | 7/1998 | Kurtz et al. | |
| 5,811,814 A | 9/1998 | Leone et al. | |
| 5,821,541 A | 10/1998 | Tümer | |
| 5,833,603 A | 11/1998 | Kovacs et al. | |
| 5,842,977 A | 12/1998 | Lesho et al. | |
| 5,846,513 A | 12/1998 | Carroll et al. | |
| 5,857,463 A | 1/1999 | Thurston et al. | |
| 5,871,013 A | 2/1999 | Wainer et al. | |
| 5,880,475 A | 3/1999 | Oka et al. | |
| 5,900,533 A | 5/1999 | Chou | |
| 5,916,167 A | 6/1999 | Kramer et al. | |
| 5,928,150 A | 7/1999 | Call | |
| 5,932,879 A | 8/1999 | Raylman et al. | |
| 5,939,724 A | 8/1999 | Eisen et al. | |
| 5,961,457 A | 10/1999 | Raylman et al. | |
| 5,984,860 A | 11/1999 | Shan | |
| 5,987,350 A | 11/1999 | Thurston | |
| 5,993,378 A | 11/1999 | Lemelson | |
| 6,002,480 A | 12/1999 | Izatt et al. | |
| 6,076,009 A | 6/2000 | Raylman et al. | |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,147,353 A | 11/2000 | Gagnon et al. | |
| 6,173,201 B1 | 1/2001 | Front | |
| 6,205,347 B1 | 3/2001 | Morgan et al. | |
| 6,212,423 B1 | 4/2001 | Krakovitz | |
| 6,236,880 B1 | 5/2001 | Raylman et al. | |
| 6,240,312 B1 | 5/2001 | Alfano et al. | |
| 6,242,743 B1 | 6/2001 | DeVito | |
| 6,246,901 B1 * | 6/2001 | Benaron | 600/431 |
| 6,261,562 B1 | 7/2001 | Xu et al. | |
| 6,263,229 B1 | 7/2001 | Atalar et al. | |
| 6,271,524 B1 | 8/2001 | Wainer et al. | |
| 6,271,525 B1 | 8/2001 | Majewski et al. | |
| 6,280,704 B1 | 8/2001 | Schutt et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,368,331 B1 * | 4/2002 | Front et al. | 606/130 |
| 6,407,391 B1 | 6/2002 | Mastrippolito et al. | |
| 6,420,711 B2 | 7/2002 | Tuemer | |
| 6,426,917 B1 | 7/2002 | Tabanou et al. | |
| 6,429,431 B1 | 8/2002 | Wilk | |
| 6,431,175 B1 | 8/2002 | Penner et al. | |
| 6,438,401 B1 * | 8/2002 | Cheng et al. | 600/407 |
| 6,453,199 B1 | 9/2002 | Kobozev | |
| 6,459,925 B1 * | 10/2002 | Nields et al. | 600/427 |
| 6,480,732 B1 * | 11/2002 | Tanaka et al. | 600/425 |
| 6,510,336 B1 | 1/2003 | Daghighian et al. | |
| 6,516,213 B1 | 2/2003 | Nevo | |
| 6,525,320 B1 | 2/2003 | Juni | |
| 6,525,321 B2 | 2/2003 | Juni | |
| 6,549,646 B1 | 4/2003 | Yeh et al. | |
| 6,560,354 B1 * | 5/2003 | Maurer et al. | 382/131 |
| 6,567,687 B2 | 5/2003 | Front et al. | |
| 6,584,348 B2 | 6/2003 | Glukhovsky | |
| 6,587,710 B1 | 7/2003 | Wainer | |
| 6,592,520 B1 | 7/2003 | Peszynski et al. | |
| 6,602,488 B1 | 8/2003 | Daghighian | |
| 6,607,301 B1 | 8/2003 | Glukhovsky et al. | |
| 6,611,141 B1 | 8/2003 | Schulz et al. | |
| 6,614,453 B1 | 9/2003 | Suri et al. | |
| 6,628,983 B1 | 9/2003 | Gagnon | |
| 6,628,984 B2 | 9/2003 | Weinberg | |
| 6,632,216 B2 | 10/2003 | Houzego et al. | |
| 6,638,752 B2 | 10/2003 | Contag et al. | |
| 6,643,538 B1 | 11/2003 | Majewski et al. | |
| 6,662,036 B2 | 12/2003 | Cosman | |
| 6,680,750 B1 | 1/2004 | Tournier et al. | |
| 6,728,583 B2 | 4/2004 | Hallett | |
| 6,748,259 B1 | 6/2004 | Benaron et al. | |
| 6,963,770 B2 | 11/2005 | Scarantino et al. | |

| | | |
|---|---|---|
| 7,043,063 B1 | 5/2006 | Noble et al. |
| 7,176,466 B2 | 2/2007 | Rousso et al. |
| 2002/0072784 A1 | 6/2002 | Sheppard et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0103431 A1 | 8/2002 | Toker et al. |
| 2002/0148970 A1 | 10/2002 | Wong et al. |
| 2002/0168317 A1 | 11/2002 | Daighighian et al. |
| 2002/0183645 A1 | 12/2002 | Nachaliel |
| 2003/0001837 A1 | 1/2003 | Baumberg |
| 2003/0013966 A1 | 1/2003 | Barnes et al. |
| 2003/0063787 A1 | 4/2003 | Natanzon et al. |
| 2003/0081716 A1 | 5/2003 | Tumer |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0054248 A1 | 3/2004 | Kimchy et al. |
| 2004/0054278 A1 | 3/2004 | Kimchy et al. |
| 2004/0086437 A1 | 5/2004 | Jackson et al. |
| 2004/0101176 A1 | 5/2004 | Mendonca et al. |
| 2004/0116807 A1 | 6/2004 | Amrami et al. |
| 2004/0204646 A1 | 10/2004 | Nagler et al. |
| 2005/0020915 A1 | 1/2005 | Bellardinelli et al. |
| 2005/0055174 A1 | 3/2005 | David et al. |
| 2006/0160157 A1 | 7/2006 | Zuckerman |
| 2007/0166277 A1 | 7/2007 | McManus et al. |
| 2008/0033291 A1 | 2/2008 | Rousso et al. |
| 2008/0230705 A1 | 9/2008 | Rousso et al. |
| 2008/0260228 A1 | 10/2008 | Dichterman et al. |

FOREIGN PATENT DOCUMENTS

| | | |
|---|---|---|
| DE | 19815362 | 10/1999 |
| EP | 0543626 | 5/1993 |
| EP | 0697193 | 2/1996 |
| GB | 2031142 | 4/1980 |
| JP | 6-109848 | 4/1994 |
| WO | WO 92/00402 | 9/1992 |
| WO | WO 99/03003 | 1/1999 |
| WO | WO 99/30610 | 6/1999 |
| WO | WO 99/39650 | 8/1999 |
| WO | WO 00/31522 | 2/2000 |
| WO | WO 00/22975 | 4/2000 |
| WO | WO 00/18294 | 6/2000 |
| WO | WO 01/89384 | 11/2001 |
| WO | WO 02/58531 | 1/2002 |
| WO | WO 02/16965 | 2/2002 |
| WO | WO 2004/042546 | 5/2004 |
| WO | WO 2006/042077 | 4/2006 |
| WO | WO 2006/129301 | 12/2006 |

OTHER PUBLICATIONS

Bromiley et al. "Attenuation Correction in PET Using Consistency Conditions and A Three-Dimensional Template", IEEE Transactions on Nuclear Science, 48(4): 1371-1377, 2001. p. 1376, col. 2, § 2.
Hayakawa et al. "A PET-MRI Registration Technique for PET Studies of the Rat Brain", Nuclear Medicine & Biology, 27: 121-125, 2000. p. 121, col. 1.
Lavallée et al. "Building A Hybrid Patient's Model for Augmented Reality in Surgery: A Registration Problem", Computing in Biological Medicine, 25(2): 149-164, 1995. p. 149-150.
Kojima et al. "Quantitative Planar Imaging Method for Measurement of Renal Activity by Using A Conjugate-Emission Image and Transmission Data", Medical Physics, 27(3): 608-615, 2000. p. 608.
Pardridge et al. "Tracer Kinetic Model of Blood-Brain Barrier Transport of Plasma Protein-Bound Ligands", Journal of Clinical Investigation, 74: 745-752, 1984.
Reutter et al. "Direct Least Squares Estimation of Spatiotemporal Distributions From Dynamic SPECT Projections Using A Spatial Segmentation and Temporal B-Splines", IEEE Transactions on Medical Imaging, 19(5): 434-450, 2000.
Huesman et al. "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45(6): 3007-3013, 1998.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Piperno et al. "Breast Cancer Screening by Impedance Measurements", Frontiers Med. Biol. Engng., 2(2): 11-17, 1990.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflammation", The Lancet, 354: 765-770, 1999.
Mori et al. "Overexpression of Matrix Metalloproteinase-7mRNA in Human Colon Carcinomas", Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Day et al. "Localization of Radioiodinated Rat Fibrogen in Transplanted Rat Tumors", J. Nat. Cancer Inst., 23: 799-812, 1959.
Jeanguillaume et al. "From the Whole-Body Counting to Imaging: The Computer Aided Collimation Gamma Camera Project (CACAO)", Radiation Projection Dosimetry 89(3-4): 349-352, 2000.
Quartuccia et al. "Computer Assisted Collimation Gama Camera: A New Approach to Imaging Contaminated Tissues", Radiation Projection Dosimetry 89(3-4): 343-348, 2000.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Hassan et al. "A Radiotelemetry Pill for the Measurement of Ionising Radiation Using A Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Zhang et al. "An Innovative High Efficiency and High Resolution Probe for Prostate Imaging", The Journal of Nuclear Medicine, 68: 18, 2000. Abstract.
Final OA dated Jul. 12, 2007.
Invitation To Pay Additional Fees.
Invitation to pay additional fees dated Apr. 18, 2007.
OA of Jun. 1, 2006.
OA of Aug. 10, 2007.
OA of Jan. 17, 2006.
OA of Jun. 19, 2006.
OA of Jan. 7, 2009.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Apr. 15, 2008 From the US Patent and Trademark Office Re.: U.S. Appl. No. 09/727,464.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Apr. 20, 2006 From the US Patent and Trademark Office Re.: U.S. Appl. No. 10/240,239.

Official Action Dated Dec. 23, 2008 From the US Patent and Trademark Office Re.: U.S. Appl. No. 09/727,464.
Official Action Dated Jun. 23, 2006 From the US Patent and Trademark Office Re.: U.S. Appl. No. 09/727,464.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report dated Sep. 12, 2002 from the International Searching Authority of the Patent Cooperation Treaty Re: Application No. PCT/IL02/00057.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Official Action Dated Dec. 16, 2008 From the US Patent and Trademark Office Re.: Application No. 10/343,792.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Aug. 14, 2008 to Official Action of Apr. 15, 2008 From the US Patent and Trademark Office Re.: U.S. Appl. No. 09/727,464.
Response Dated Nov. 25, 2005 to Office Action of May 13, 2005 From the Patent Office of the People's Republic of China Re.: Application No. 1817689.5.
Response to the International Search Report and the Written Opinion of Oct. 10, 2006 From the International Searching Authority Re.: Appliction No. PCT/IL06/00059.
Summons to Attend Oral Proceedings Pursuant to Rule 115(1) EPC Dated Jan. 16, 2009 From the European Patent Office Re.: Application No. 03810570.6.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperatin Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215 .
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperatin Treaty Re.: Application No. PCT/IL03/00917.
International Searching Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.

Office Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Jul. 2, 2007 From the International Searching Authority of the Patent Cooperation Treaty Re.: Application No. PCT/IL2006/001291.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575..
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording The Ionizing Radiation In The Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.

Official Action Dated Jan. 7, 2009 From the US Patent and Trademark Office Re.: U.S. Appl. No. 10/616,307.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for A Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Bromiley et al: "Attenuation Correction in PET Using Consistency Conditions and A Three-Dimensional Template", IEEE Transactions on Nuclear Science, XP002352920, 48(4): 1371-1377, 2001.
Kojima et al: "Quantitative Planar Imaging Method for Measurement of Renal Activity by Using A Conjugate-Emission Image and Transmission Data", Medical Physics, 27(3): 608-615, 2000.
Notice of Allowance Dated Jul. 16, 2009 From the US Patent and Trademark Office Re.: U.S. Appl. No. 12/084,559.
Official Action Dated Jul. 15, 2009 From the US Patent and Trademark Office Re.: U.S. Appl. No. 10/616,301.
Official Action Dated Jul. 20, 2009 From the US Patent and Trademark Office Re.: U.S. Appl. No. 11/980,617.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.

* cited by examiner

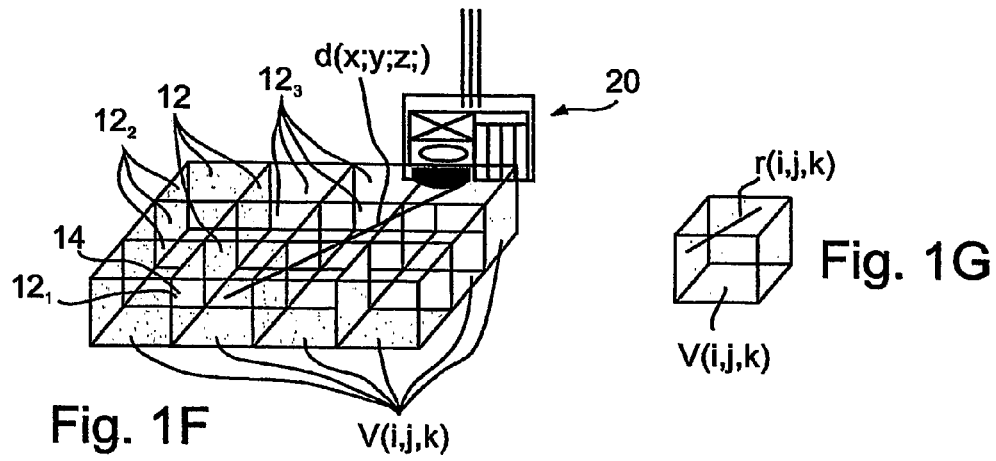
Fig. 1F
Fig. 1G
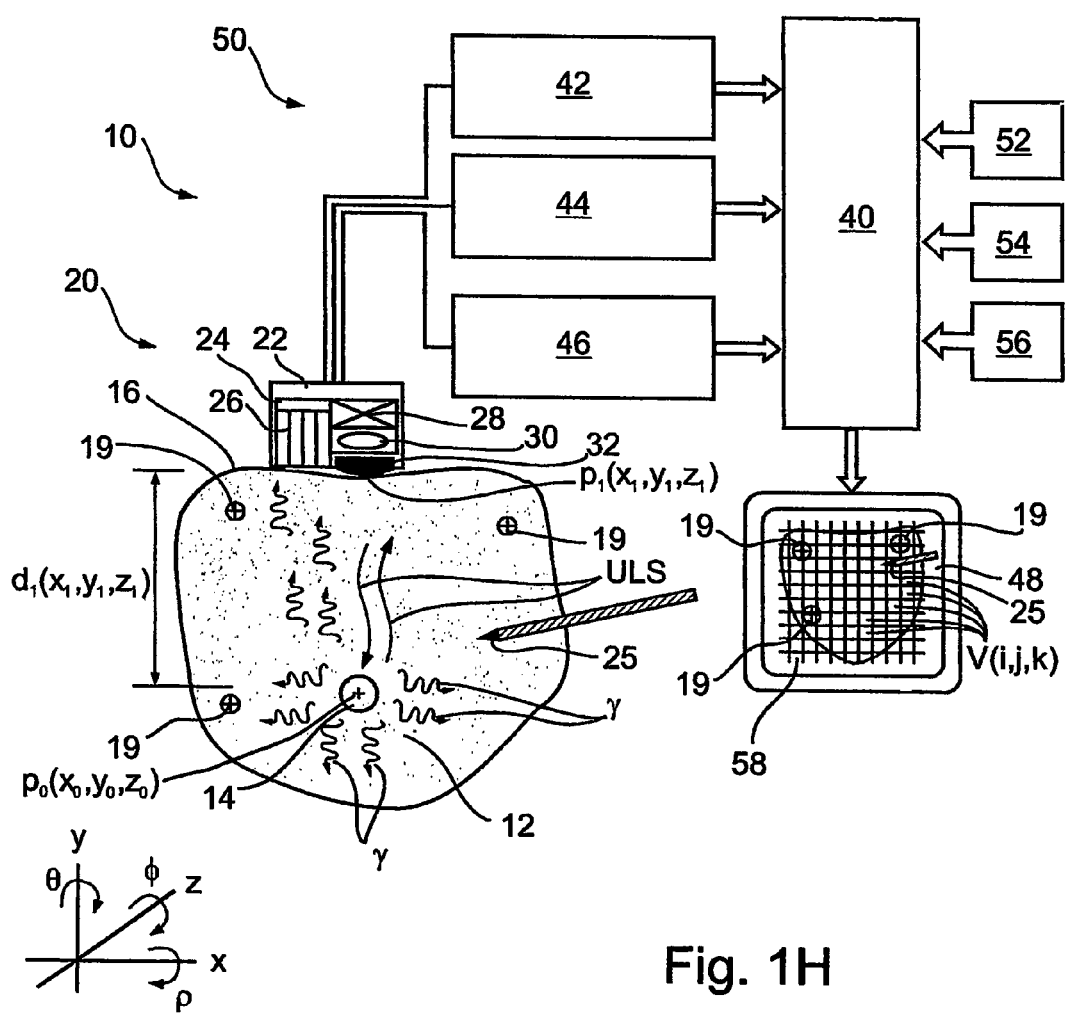
Fig. 1H

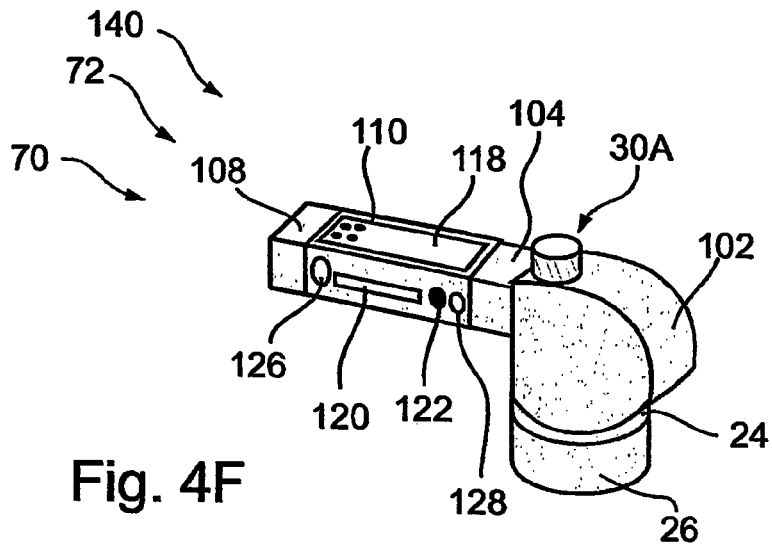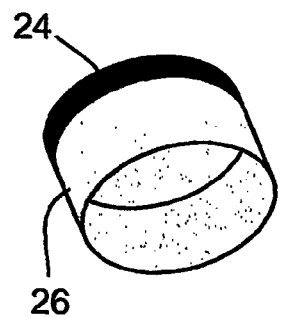
Fig. 4F
Fig. 4G
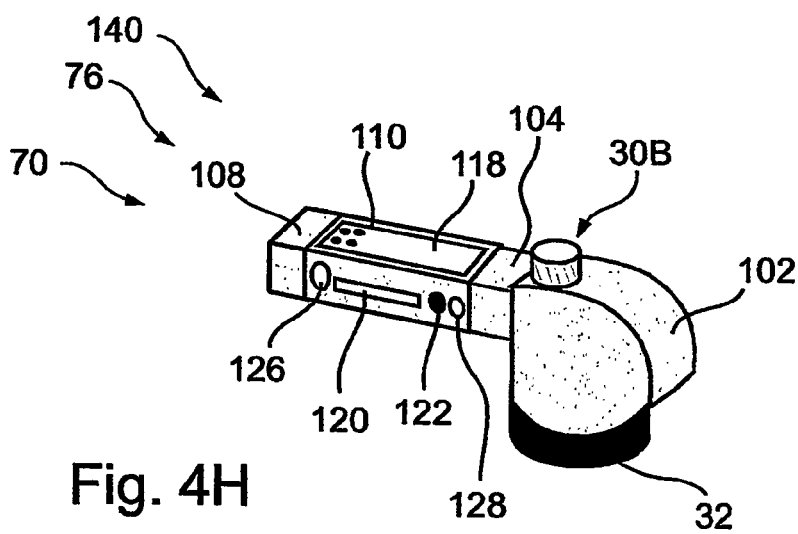
Fig. 4H
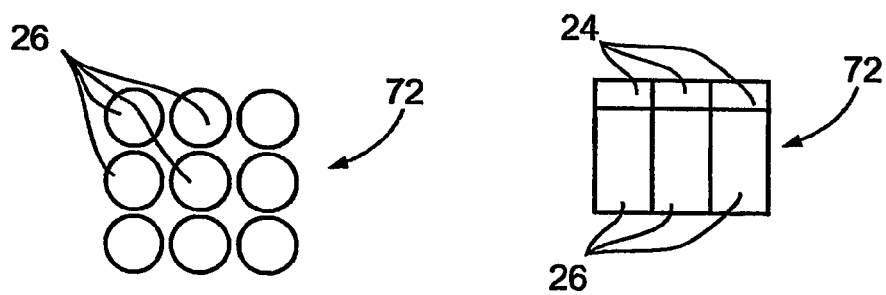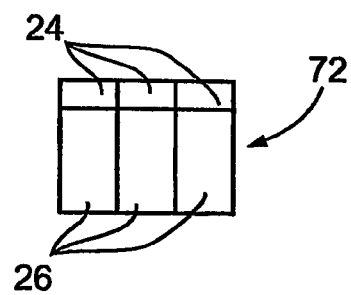
Fig. 4I
Fig. 4J

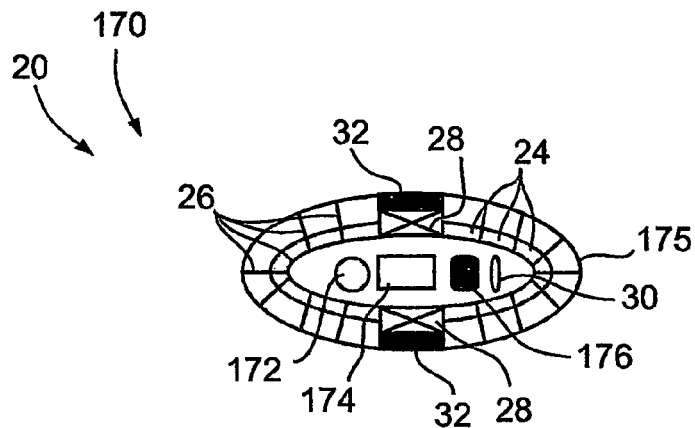
Fig. 9A
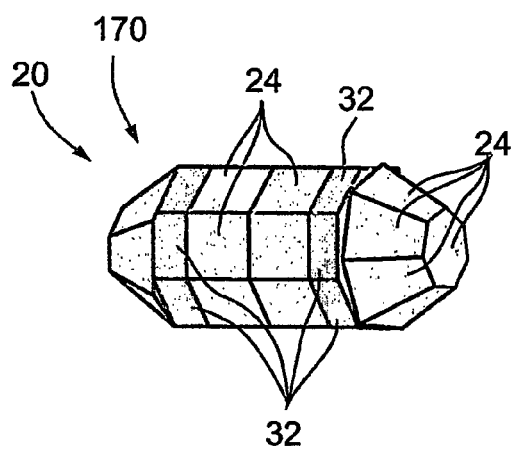
Fig. 9B
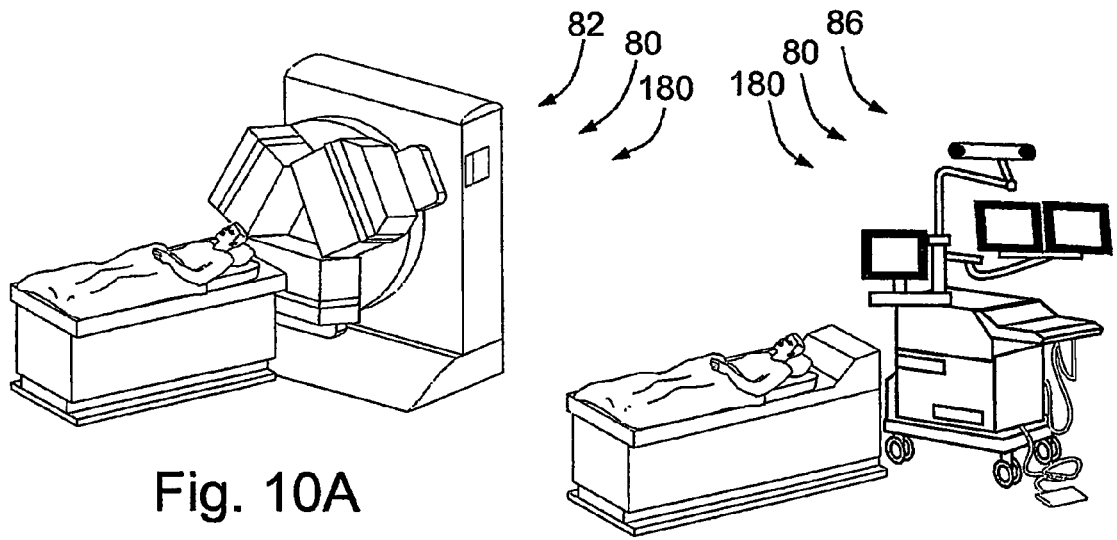
Fig. 10A
Fig. 10B

APPARATUS AND METHODS FOR IMAGING AND ATTENUATION CORRECTION

CROSS REFERENCE TO RELATED PATENT APPLICATIONS

This application is a National Phase Application of PCT/IL03/00917 having International Filing Date of 4 Nov. 2003, which claims benefit of from U.S. Provisional Patent Application No. 60/423,359 filed 4 Nov. 2002, and from U.S. patent application Ser. No. 10/616,307 filed 10 Jul. 2003, and from U.S. patent application Ser. No. 10/616,301 filed 10 Jul. 2003.

FIELD AND BACKGROUND OF THE INVENTION

The present invention relates to the integration of nuclear-radiation imaging, on the one hand, with ultrasound or magnetic resonance imaging, on the other, in order to superimpose the two images, and in order to utilize the structural information of the ultrasound or magnetic resonance for attenuation correction of the nuclear-radiation image.

In essence, two types of medical images may be distinguished:
1. functional body images, such as may be produced by gamma camera, SPECT, and PET scans, which provide physiological information; and
2. structural images, such as may be produced by as x-ray, CT, ultrasound, and (or) MRI scans, which provide anatomic, or structural maps of the body.

A functional image shows the metabolic activity of body tissue, since dead or damaged body tissue absorbs radiopharmacueticals at a different rate from a healthy tissue. For example, a functional image may be used for in-vivo measurements of cardiac rhythm or respiratory rhythm, quantitation of tissue metabolism and blood flow, evaluation of coronary artery disease, quantitation of receptor binding, measurement of brain perfusion, and liver imaging. Additionally, since the uptake rate of radiopharmacueticals is different between healthy tissue and a tumor, and is furthermore different between malignant and benign portions of a tumor, functional images are of importance in tumor localization and volume determination, and especially, localization and volume determination of malignant portions of tumors. However, a functional image may not show structural details.

On the other hand, a structural image reveals almost exclusively structural details—an anatomic map, for example, by distinguishing bones from soft tissue.

Techniques for registering functional and structural images on a same system of coordinates, to produce a combined, or fused image, are known, and are disclosed, for example in the publication to D. A. Weber and M. Ivanovic, "Correlative image registration", Sem. Nucl. Med., vol. 24 pp. 311-323 (1994), as well as in K. Kneöaurek, M. Ivanovic, J. Machac, and D. A. Weber, "Medical image registration," Europhysics News (2000) Vol. 31 No. 4, in U.S. Pat. No. 6,212,423, to Krakovitz, dated, Apr. 3, 2001, and entitled Diagnostic hybrid probes, in U.S. Pat. No. 5,672,877, to Liebig, et al., dated Sep. 30, 1997 and entitled, "Coregistration of multi-modality data in a medical imaging system," in U.S. Pat. No. 6,455,856, to Gagnon, dated, Sep. 24, 2002 and entitled, "Gamma camera gantry and imaging method," and in commonly owned U.S. Pat. No. 6,567,687, to front et al., issued on May 20, 2003, and entitled, "Method and system for guiding a diagnostic or therapeutic instrument towards a target region inside the patient's body," all of whose disclosures are incorporated herein by reference.

These techniques may be used, for example, in order to identify features seen on the functional map, based on their anatomic location in the structural map, for example, for the study of cardiac rhythm, or respiratory rhythm.

However, when raw radioactive emission data is superimposed on a structural image, the resultant image fusion may be somewhat erroneous, due to tissue attenuation. Attenuation refers to "the inevitable loss of information in an image due to the interaction of emitted photons with matter, through photon absorption by the photoelectric effect, photon scatter, by the Compton effect, and pair production, involving photons of energies greater than 1.02 Mev. Attenuation decreases the number of photon counts from that which would have been recorded in vacuum. The relative probability of one of these interactions to occur is a function of the incident photon energy and the atomic number (Z) of the interacting matter.

In functional imaging, a radionuclide or a compound labeled with a radionuclide is injected into a subject. The radiolabelled material concentrates in an organ or lesion of interest, and can show a concentration defect. At a prescribed time following injection, the pattern of concentration of the radiolabelled material is imaged by a radioactive emission detector, such as rectilinear scanner, scintillation camera, single-photon emission computed tomography (SPECT) system, or positron emission tomography (PET) system.

The radionuclide imaging procedure requires a means to define the path along which the emitted gamma-ray travels before striking the detector of the imaging system. The path can be a vector path, a line, narrow fan, or a narrow cone as defined by the detector or collimator. In rectilinear scanners, scintillation cameras, and SPECT systems, a collimator (typically made of lead or other high-atomic number material) is interposed between the object and the detector to define the gamma-ray path. In PET, the unique characteristics of positron annihilation radiation are coupled with electronic circuitry to define the vector path. In all cases, the only information obtained when a gamma-ray strikes the detector is the fact that the photon originated somewhere within the object along the vector path projected back from the detector.

For projection imaging systems, a two-dimensional image is formed with the intensity of each picture element, or pixel, proportional to the number of photons striking the detector at that position. In SPECT or PET, the vector paths are determined for multiple projection positions, or views, of the object, and cross-sectional or tomographic images are reconstructed of the object using standard algorithms. Again, the intensity assigned to each vector path is proportional to the number of photons striking the detector originating along the path, and the intensity of each pixel in the reconstructed image is related to these vector path intensities obtained at multiple views.

In radionuclide imaging, it is desirable to obtain absolute values for radionuclide concentrations (or radionuclide uptake) at each point in the image. Attenuation of the emitted photons within the object, before they reach the detector, is a function of the energy of the photons and the exact composition of the material through which the photons pass to reach the detector. Photons emitted deeper within the object have a higher probability of attenuation than those emitted near the surface. In addition, the composition of the material (in terms of effective atomic number Z and electron density) affects the attenuation, with more attenuation if the path passes through high-Z or high-density regions. Thus, in order to calculate absolute uptake or concentration of a radionuclide in a region of an object, it is required that the path length of each type of material or tissue (or effective-Z and electron density path lengths) be known for each vector. Attenuation corrections for emitted photons are made from this knowledge, allowing accurate concentration values to be obtained.

The full clinical potential of radionuclide imaging has been seriously hindered by some important limitations. The spatial resolution and photon statistical limitations of radionuclide imaging frustrate accurate anatomical localization and hinder quantitation of the radionuclide distribution. Photon attenuation has been identified by the American Heart Association and leading nuclear cardiologists as a major deficiency in diagnosis of heart disease with SPECT, and is a major source of error in the measurement of tumor metabolism using radionuclide techniques. Quantitation is further complicated by the need for scatter compensation for imaging with both single-photon and positron-emitting radionuclides.

A number of researchers have shown that many of these limitations can be overcome through use of emission-transmission imaging techniques which combine anatomical (structural) information from transmission images with physiological (functional) information from radionuclide emission images. By correlating the emission and transmission images, the observer can more easily identify and delineate the location of radionuclide uptake. In addition, the quantitative accuracy of measurement of radionuclide uptake can be improved through use of iterative reconstruction methods, which can account for these errors and improve the radionuclide images.

Existing medical imaging instrumentation has been designed for either emission or transmission imaging, but not both, and attempts to perform both compromise one or both of the data sets. In addition, in the early 1990's when much of this work was done, implementation of iterative reconstruction algorithms was too slow to converge and therefore impeded the flow of information in a hospital setting. Virtually all clinical tomographic systems use analytic rather than iterative reconstruction algorithms, which, unlike iterative reconstruction techniques, have the major advantage that the image reconstruction process can occur concurrently with the acquisition of the image data. The efficiency of analytic approaches is compromised by their inability to account for the quantitative errors of photon attenuation, scatter radiation, and spatial resolution losses mentioned above.

The prior art in this field includes several different approaches to localize and quantify the uptake of radionuclides in the human body. One approach uses stereotactic techniques or computer processing methods to correlate functional information from SPECT or PET images with morphologic information from magnetic resonance imaging (MRI) or CT. This technique has the advantage that it can be applied retrospectively without acquiring new image data from the patient. However, these approaches are computationally intensive, require that the patient be scanned separately on two systems, and have only been successful in the head where the skull limits motion of internal anatomical structures.

A second set of prior art describes instrumentation used to detect emission and transmission data using instruments with single or multiple detectors. Several investigators have acquired both the emission and transmission images. with a radionuclide point, line, or sheet used as the transmission source, which is placed on the opposite side of the body from the scintillation camera. This approach has been applied more recently using SPECT. Studies have shown that this technique is capable of producing adequate attenuation maps for attenuation correction to improve quantitation of radionuclide uptake, and that some modest anatomical localization of the radionuclide distribution is also possible.

An alternative approach uses specially-designed instruments for emission-transmission imaging. For example, Kaplan (International Patent Application No. PCT/US90/03722) describes an emission-transmission system in which the emission and transmission data are acquired with the same detector (single or multiple heads). An alternative emission-transmission imaging system (disclosed in SU-1405-819-A) uses x-ray transmission data and two detectors for determining the direction of the photons to improve detection efficiency. However, an exact method of correcting emission data based on transmission data is not described by either Kaplan or in SU-1405-819-A.

Other prior art notes that the map of attenuation coefficients required for the attenuation correction procedure can be obtained from a separate x-ray transmission CT scan of the patient, although a specific method of generating an attenuation map at the photon energy of the radionuclide source is not known. Specific techniques to determine the attenuation map of the patient from single-energy transmission measurement using radionuclide or x-ray sources have been described which are limited to sources emitting monoenergetic (line) spectra rather than broad spectra such as those typically obtained from an x-ray source.

Specific algorithms for correcting beam-hardening artifacts use single-energy x-ray data and dual-energy x-ray data As used herein, the term "single-energy x-ray" describes methods in which an image is generated by integrating the x-ray signal over a single range of photon energies. As used herein, the term "dual-energy x-ray" describes methods in which two images are generated by integrating the signal over two different photon energy ranges. Thus, either "single-energy x-ray" or "dual-energy x-ray" includes methods in which the x-ray source emits an x-ray beam having either a narrow or broad spectrum of energies. Algorithms for correcting beam-hardening artifacts by using basis-material measurements derived from single-energy or dual-energy x-ray data have been presented but without describing how these measurements can be applied to correction of radionuclide data. Especially for single-energy measurements, the correction techniques associated therewith are principally directed at the removal of beam-hardening streaks and nonuniformities, which disturb the qualitative evaluation of images produced with CT.

A key element has been the combination of the emission and transmission data in a reconstruction algorithm which corrects the radionuclide distribution for photon attenuation. Several authors have described analytic algorithms such as filtered backprojection in which the radionuclide data is modified using an attenuation map to correct for attenuation errors. Among their advantages, these analytic algorithms are fast and require only a single step to reconstruct the radionuclide distribution.

However, they are inexact and utilize a uniform attenuation map in which the value of the attenuation coefficient is assumed to be constant across the patient. Other reconstruction algorithms are iterative and use an exact attenuation map and the radionuclide projection data to estimate the radionuclide distribution across the patient. Maximum likelihood estimation is one statistical method that can be used for image reconstruction. A maximum likelihood estimator appropriate for radionuclide tomography based on an iterative expectation maximization algorithm (ML-EM) has been described. The ML-EM algorithm is easy to implement, accounts for the Poisson nature of the photon counting process inherent with radionuclide imaging, and produces better images than filtered backprojection. In addition, ML-EM algorithms can incorporate physical phenomena associated with radionuclide tomography, such as photon attenuation and scatter, detection efficiency, and geometric aspects of the imaging process. Iterative weighted least squares/conjugate gradient (WLS/CG) methods have also been proposed and used for radionuclide tomography. Overall, WLS/CG reconstruction algorithms converge faster than ML-EM procedures, while still incorporating the statistical nature of radionuclide imaging, and permit compensation for photon attenuation and scatter, detection efficiency and geometric response. Iterative algorithms have been successfully used for both SPECT and PET imaging.

The major disadvantage of iterative algorithms is their computational burden, which when introduced, in the early 1990's represented a major obstacle. Iterative algorithms are iterative procedures and are started with an initial image estimate that either corresponds to a constant radionuclide density throughout the image plane to be reconstructed or corresponds to constant density throughout the highly sampled "reconstruction circle" and zero outside this region. This estimate is unlikely to be representative of the actual distribution of radionuclide in a patient, and a large fraction of the total iterations required to generate useful images may be necessary to reveal the real qualitative structure of the radionuclide distribution. Thus, these algorithms often require 30 to 50 iterations to yield visually acceptable images, and possibly several hundred iterations to generate quantitatively accurate reconstructions.

It also is possible to use filtered backprojection to produce initial image estimates for iterative reconstruction algorithms. Filtered backprojection algorithms can operate concurrently with the emission data acquisition, and they are the method currently used for most clinical radionuclide imaging systems due to their efficiency and ability to produce useful images. Unfortunately it is generally not possible to modify filtered backprojection algorithms to accurately account for details of the collimator geometry, or for the effects of scatter, especially in regions where there are large inhomogeneities in these properties, or details of the collimator geometry.

Therefore, this approach can speed up iterative techniques slightly, although the improvement in convergence speed has not been dramatic. Thus, many investigators have pursued various methods of speeding the convergence of ML-EM algorithms or reducing the time required per iteration. Methods include exploiting the symmetry of the imaging system, multigrid approaches, high frequency enhanced filtered iterative reconstruction, expectation maximization search (EMS) algorithms, rescaled gradient procedures, vector-extrapolated maximum likelihood algorithms, and hybrid maximum likelihood/weighted least squares (ML/WLS) algorithms.

However, all iterative reconstruction methods require significantly more computer time than filtered backprojection algorithms to generate useful images. The iterative ML-EM and WLS/CG algorithms mentioned above assume complete sets of radionuclide projection data exists prior to commencement of the reconstruction procedure. The requirement to acquire complete sets of projection data is especially important in radionuclide system because clinical emission imaging systems typically require several minutes to acquire projection data, making iterative reconstruction techniques impractical.

U.S. Pat. No. 5,155,365, to Cann, et al., dated Oct. 13, 1992, and entitled, Emission-transmission imaging system using single energy and dual energy transmission and radionuclide emission data." whose disclosure is incorporated herein by reference, describes a method of improving radionuclide emission imaging, by correcting emission transmission data for attenuation along calculated path lengths and through calculated basis material. Single or dual energy projector data can be simultaneously obtained with radionuclide emission data to improve localization of radionuclide uptake. Dual energy x-ray projection techniques are used to calculate the path lengths and basis material (bone, tissue, fat). The radionuclide emission data and the transmitted x-ray data are simultaneously obtained using an energy selective photon detector whereby problems of misregistration are overcome. The dual-energy x-ray projection data are utilized to determine material-specific properties and are recombined into an effectively monoenergetic image, eliminating inaccuracies in material property estimation due to beam hardening. Use of a single instrument for simultaneous data collection also reduces technician time and floor space in a hospital.

Additionally, U.S. Pat. No. 5,376,795, to Hasegawa, et al., dated Dec. 27, 1994, and entitled, "Emission-transmission imaging system using single energy and dual energy transmission and radionuclide emission data," whose disclosure is incorporated herein by reference, describes additional work, in essence, by the same group as that of U.S. Pat. No. 5,155,365, for improving radionuclide emission imaging, by correcting emission-transmission data for attenuation along calculated path lengths and through calculated basis material. X-ray transmission data are used to develop an attenuation map through an object, which is then used in reconstructing an image based on emission data. Specifically, tomographic reconstruction algorithms were used to calculate an attenuation map, which shows the distribution of attenuation coefficients at each point across the volume imaged in the patient. Radiation detection circuitry is provided which has different operating modes in detecting the x-ray and emission photons passing through the object. An iterative process is used to reconstruct the radionuclide distribution using the radionuclide projection data and the attenuation map based on physical characteristics of the object being imaged. Subsets of the complete radionuclide projection data are used to reconstruct image subsets of the radionuclide distribution. The image subsets can be generated concurrently with the acquisition of the radionuclide projection data or following acquisition of all data.

U.S. Pat. No. 5,210,421, to Gullberg, et al., dated May 11, 1993, and entitled, "Simultaneous transmission and emission converging tomography, whose disclosure is incorporated herein by reference discloses a SPECT system which includes three gamma camera heads which are mounted to a gantry for rotation about a subject. The subject is injected with a source of emission radiation, which emission radiation is received by the camera heads. A reconstruction processor reconstructs the emission projection data into a distribution of emission radiation sources in the subject. Transmission radiation from a radiation source passes through the subject and is received by one of the camera heads concurrently with the emission radiation. The transmission radiation data is reconstructed into a three-dimensional CT type image representation of radiation attenuation characteristics of each pixel of the subject. An attenuation correction processor corrects the emission projection data to compensate for attenuation along the path or ray that it traversed. In this manner, an attenuation corrected distribution of emission sources is generated.

Additionally, U.S. Pat. No. 5,338,936, also to Gullberg, et al., dated Aug. 16, 1994, and entitled, "Simultaneous transmission and emission converging tomography," whose disclosure is incorporated herein by reference, discloses a SPECT system, which includes three gamma camera heads, which are mounted to a gantry for rotation about a subject. The subject is injected with a source of emission radiation, which emission radiation is received by the camera heads. Transmission radiation from a transmission radiation source is truncated to pass through a central portion of the subject but not peripheral portions and is received by one of the camera heads concurrently with the emission data. As the heads and radiation source rotate, the transmitted radiation passes through different parts or none of the peripheral portions at different angular orientations. An ultrasonic range arranger measures an actual periphery of the subject. Attenuation properties of the subject are determined by reconstructing (90") the transmission data using an iterative approximation technique and the measured actual subject periphery. The actual periphery is used in the reconstruction process to reduce artifacts attributable to radiation truncation and the associated incomplete sampling of the peripheral portions. An emission reconstruction processor reconstructs the emission projection data and attenuation properties into an attenuation corrected distribution of emission radiation sources in the subject.

Furthermore, U.S. Pat. No. 5,559,335, to Zeng and Gullberg, dated Sep. 24, 1996, and entitled, "Rotating and warping projector/backprojector for converging-beam geometries," a detector head which receives emission radiation projections from the radioisotope with which a subject was injected, and transmission radiation projections from a transmission radiation source disposed opposite the subject from the detector head. A volume memory stores an estimated volume image. For each actually collected image emission data projection set, a projector reprojects a set of projection of the volume image from the image memory along each of the same projection directions as the emission data projections. Each projection is rotated and warped such that rays, which converge with the same angle as the convergence of the collimator on the detector head become parallel. The layers are each convolved with a point response function weighted in accordance with a depth of the corresponding layer in the volume image and corresponding points are summed to create a reprojected projection. A ratio of each collected projection and the reprojected projection is calculated and backprojected into a volume of correction factors. The backprojectioned correction factors for the set of ratios are summed. A memory-updating algorithm multiplies the estimated volume image in the image memory by the sum of the correction factors. This process is repeated iteratively over a plurality of projection directions, each iteration further refining the volume image in the volume image memory.

U.S. Pat. No. 5,672,877, to Liebig, et al., dated Sep. 30, 1997, and entitled, "Coregistration of multi-modality data in a medical imaging system," whose disclosure is incorporated herein by reference, discloses a method of coregistering medical image data of different modalities. In the method, an emission scan of an object is performed using a nuclear medicine imaging system to acquire single-photon emission computed tomography (SPECT) image data. A transmission scan of the object is performed simultaneously with the emission scan using the same nuclear medicine imaging system in order to acquire nuclear medicine transmission image data. The emission scan is performed using a roving zoom window, while the transmission scan is performed using the full field of view of the detectors. By knowing the position of the zoom windows for each detection angle, the nuclear medicine transmission image data can be coregistered with the SPECT emission image data as a result of the simultaneous scans. Image data of a modality other than SPECT, such as x-ray computed tomography (x-ray CT) data, magnetic resonance imaging (MRI) data, or positron emission tomography (PET) data, is also provided, which it is desired to have coregistered with the SPECT emission data. The nuclear medicine transmission image data is therefore coregistered with the image data of the different modality. As a result, the image data of the different modality becomes coregistered with the SPECT image data.

U.S. Pat. No. 6,310,968, to Hawkins, et al., dated Oct. 30, 2001, and entitled, "Source-assisted attenuation correction for emission computed tomography," whose disclosure is incorporated herein by reference, discloses a method of ML-EM image reconstruction, for use in connection with a diagnostic imaging apparatus that generates projection data. The method includes collecting projection data, including measured emission projection data. An initial emission map and attenuation map are assumed. The emission map and the attenuation map are iteratively updated. With each iteration, the emission map is recalculated by taking a previous emission map and adjusting it based upon: (i,j,k) the measured emission projection data; (ii) a reprojection of the previous emission map which is carried out with a multi-dimensional projection model; and, (iii) a reprojection of the attenuation map. As well, with each iteration, the attenuation map is recalculated by taking a previous attenuation map and adjusting it based upon: (i,j,k) the measured emission projection data; and, (ii) a reprojection of the previous emission map which is carried out with the multi-dimensional projection model. In a preferred embodiment, with source-assisted reconstruction, the recalculation of the attenuation map is additionally based upon: (iii) measured transmission projection data; and, (iv) a reference or blank data set of measured transmission projection data taken without the subject present in the imaging apparatus.

Additionally, U.S. Pat. No. 6,339,652, also to Hawkins, et al., dated Jan. 15, 2002, and entitled, "Source-assisted attenuation correction for emission computed tomography," whose disclosure is incorporated herein by reference, discloses a method of ML-EM image reconstruction, for use in connection with a diagnostic imaging apparatus that generates projection data. The method includes collecting projection data, including measured emission projection data and measured transmission projection data. Optionally, the measured transmission projection data is truncated. An initial emission map and attenuation map are assumed. The emission map and the attenuation map are iteratively updated. With each iteration, the emission map is recalculated by taking a previous emission map and adjusting it based upon: (i,j,k) the measured emission projection data; (ii) a reprojection of the previous emission map which is carried out with a multi-dimensional projection model; and, (iii) a reprojection of the attenuation map. As well, with each iteration, the attenuation map is recalculated by taking a previous attenuation map and adjusting it based upon: (i,j,k) the measured emission projection data; (ii) a reprojection of the previous emission map which is carried out with the multi-dimensional projection model; and (iii) measured transmission projection data.

U.S. Pat. No. 6,384,416, to Turkington, et al., et al, dated May 7, 2002, and entitled, "Transmission scanning technique for gamma-camera coincidence imaging," whose disclosure is incorporated herein by reference, discloses gamma-camera coincidence (GCC) imaging systems and methods, which include a pair of gamma camera imaging heads rotatable about a patient-longitudinal imaging axis. The imaging heads each has a plurality of radiation opaque septa plates extending transversely relative to the imaging axis about which they locate. Adjacent ones of the septa plates are spaced apart along the imaging axis. At least one point source of radiation is thus positionally fixed between a predetermined adjacent pair of the septa plates of one of the imaging heads so as to be concurrently rotatable therewith.

U.S. Pat. No. 6,384,416, hereinabove, further discloses a method of obtaining attenuation map images by gamma-camera coincidence imaging comprising the steps of:

(a) positionally fixing a radiation point source having a radiation energy greater than about 511 KeV between an adjacent pair of plate-shaped radiation opaque septa of one gamma camera imaging head laterally of a patient-longitudinal imaging axis near a diagonal plane extending along the imaging axis between the one imaging head and an oppositely opposed another gamma camera imaging head;

(b) injecting a human or animal subject with a radiopharmaceutical;

(c) conducting a transmission scan by rotating the one gamma camera imaging bead concurrently with the oppositely opposed another gamma camera imaging head about the patient-longitudinal longitudinal imaging axis so that the another gamma camera imaging head acquires transmission scan data therefrom;

(d) conducting an emission coincidence imaging scan of the subject to obtain emission scan data therefrom; and (e) combining the transmission and emission scan data to obtain attenuation-corrected cross-sectional maps of radioactivity distributions.

U.S. Pat. No. 6,429,434, to Watson, et al., dated Aug. 6, 2002, and entitled, "Transmission attenuation correction method for PET and SPECT," whose disclosure is incorporated herein by reference, discloses a transmission source, which serves to detect activity from a radiation source for correcting attenuation in either PET mode or SPECT mode. The transmission source includes a detector dedicated to collecting attenuation data in PET mode. A collimated radiation source and a detector are positioned with respect to a tomography device such that only a selected strip of the imaging detector of the tomograph is illuminated such that events unrelated to the attenuation are eliminated. The transmission source can either be a coincidence transmission source or a singles transmission source and includes a collimator in which is disposed a radiation source. An opening is defined by the collimator for exposing a selected portion of the imaging detectors of the tomograph device. Positioned behind the radiation source, relative to the imaging detectors, is the dedicated attenuation detector. In a dual head tomograph device, one transmission source of the present invention is disposed opposite each bank of imaging detectors. The sources and the associated collimators are positioned to the side of each head at a slight angle relative to the respective head. The sources and detectors are fixed relative to the imaging heads. In order to obtain full coverage of the field of view (FOV) in the same manner as for an emission scan, the heads and sources are rotated about the center of the camera. In SPECT mode, the point source is selected to have sufficiently high energy to shine through the patient and the collimators associated with the imaging detector.

U.S. Pat. No. 6,455,856, to Gagnon, dated, Sep. 24, 2002, and entitled, "Gamma camera gantry and imaging method," whose disclosure is incorporated herein by reference, discloses a gamma camera, which includes first and second detectors. The first detector is located beneath a patient's receiving surface. The second detector is located above the patient's receiving surface. The second detector is movable between operating and retracted positions. The second detector includes a plurality of discrete detector portions, each detector portion having a first radiation sensitive face, which faces an examination region and a second radiation sensitive face. The patient receiving surface generates signals indicative of pressure applied to the patient receiving surface. A movable transmission radiation source provides transmission radiation, interactions between the transmission radiation and the second detector generating Compton scattered radiation at least a portion of which is received by the first detector, coincident radiation being used to generate a transmission attenuation map. The gamma camera also includes an ultrasound device.

U.S. Pat. No. 6,539,103, to Panin, et al., dated Mar. 25, 2003, and entitled, "Method and apparatus for image reconstruction using a knowledge set," whose disclosure is incorporated herein by reference discloses a method of constructing a non-uniform attenuation map of a subject for use in image reconstruction of SPECT data is provided. It includes collecting a population of a priori transmission images and storing them in an a priori image memory. The transmission images are not of the subject. Next, a cross-correlation matrix is generated from the population of transmission images. The eigenvectors of the cross-correlation matrix are calculated. A set of orthonormal basis vectors is generated from the eigenvectors. A linear combination of the basis vectors is constructed, and coefficients for the basis vectors are determined such that the linear combination thereof defines the non-uniform attenuation map.

A. J. Nygren published in May 1997, in web page www Dot owlnet Dot rice Dot edu/~elec539/Projects97/cult/node8 dot html a method for an exact attenuation correction, using algebraic reconstruction. Nygren assumed that an attenuation profile of the object being imaged is known. The reconstruction problem is then formulated with pixel weights assigned by a projection operator, which depends on the distance between the pixel and the detector, and on the assumed attenuation profile. Unlike Chang's method, which involves averaging correction factors, this method allows an exact attenuation correction, using algebraic reconstruction methods.

Other publications include, for example, J.-M. Wagner, F. Noo, R. Clackdoyle, G. Bal, and P. Christian, "Attenuation Correction for Rotating Slant-Hole (RSH)SPECT using Exact Rebinning," in Conference Record of the 2001 IEEE Nuclear Symposium and Medical Imaging Conference, IEEE Catalog Number 0-7803-7324-3 abstract number M8-5, San Diego, USA, November 2002, and F. Noo, R. Clackdoyle, and J.-M. Wagner, "3D Image Reconstruction from Exponential X-ray Projections: a Completeness Condition and an inversion Formula," in Conference Record of the 2001 IEEE Nuclear Symposium and Medical Imaging Conference, IEEE Catalog Number 0-7803-7324-3, abstract number M9C-4, San Diego, USA, November 2002.

Additionally, M. P. Tornai, et al, published in web page www-mfk Dot hitachi-medical Dot co dot jp/mfk/medix/29_05 dot pdf "Investigation of Large Field-of View Transmission Imaging for Non-uniform-Attenuation Compensation in Cardiac SPECT. Part 1, Phantom Studies. Their results showed that the implementation of Transmission computed Topography (TCT) acquisition, combined with Non-Uniform Attenuation maps (NUA) compensation techniques, which utilized iterative reconstruction algorithms were promising, and yielded suitable compensated images.

In contrast to these, Chang's Attenuation Correction is a simple approach, described in web page 23ku Dot net/~chiba-kakugi/kiso/chang Dot html, The Society of Nuclear Medicine Technology in CHINA, which involves averaging correction factors, so as to use a single attenuation correction value for the tissue.

However, the aforementioned patents and publications suffer from a basic drawback. They attempt to arrive at an attenuation correction factor for gamma rays, using data obtained from x-rays, which are in essence, the same kind of radiation. Therefore, these methods are iterative by nature.

Ultrasound or ultrasonography is a medical imaging technique that uses high frequency sound waves in the range of 1 to 5 megahertz, and their echoes. The sound waves travel in the body and are reflected by boundaries between different types of tissues, such as between a fluid and a soft tissue, or between a soft tissue and a bone). The reflected waves are picked up by the ultrasound probe, and the ultrasound instrumentation calculates the distance from the probe to the reflecting boundary, based on the speed of sound in tissue (about 540 m/s) and based on the of travel, which is usually measured in millionths of a second. The distances and intensities of the echoes are displayed on the screen, forming a two-dimensional image.

In a typical ultrasound, millions of pulses and echoes are sent and received each second. The probe can be moved along the surface of the body and angled to obtain various views.

Before the early 1970's ultrasound imaging systems were able to record only the strong echoes arising from the outlines of an organ, but not the low-level echoes of the internal structure. Therefore liver scans, for instance, did not show possible carcinomas or other pathological states. In 1972 a refined imaging mode was introduced called gray-scale display, in which the internal texture of many organs became visible. In gray-scale display, low-level echoes are amplified and recorded together with the higher-level ones, giving many degrees of brightness. In consequence, ultrasound imaging became a useful tool for imaging tumors, for example, in the liver.

A development of recent years is 3D ultrasound imaging, in which, several two-dimensional images are acquired by moving the probes across the body surface or by rotating probes, inserted into body lumens. The two-dimensional scans are then combined by specialized computer software to form 3D images.

Ultrasound probes, are formed of piezoelectric crystals, which produce an electric signal in response to a pressure pulse, and come in many shapes and sizes. The shape of the probe determines its field of view, and the frequency of emitted sound determines the depth of penetration. Generally, the probes are designed to move across the surface of the body, but some probes are designed to be inserted through body lumens, such as the vagina or the rectum, so as to get closer to the organ being examined.

In multiple-element probes, each element has a dedicated electric circuit, so that the beam can be "steered" by changing the timing in which each element sends out a pulse. Additionally, transducer-pulse controls allow the operator to set and change the frequency and duration of the ultrasound pulses, as well as the scan mode of the machine. A probe formed of array transducers has the ability to be steered as well as focused. By sequentially stimulating each element, the beams can be rapidly steered the from left to right, to produce a two-dimensional cross sectional image.

Several modes of operation are known, A-mode, B-mode, Compounded B-mode, and M-mode or Real-Time mode.

The earliest was the A-mode. Originally when a sound pulse was received it was processed to appear as a vertical reflection of a point. It looked like spikes of different heights. The intensity of the returning pulse determined the height of the vertical reflection and the time it took for the impulse to make the round trip determined the space between vertical reflections. This method of display was called A-mode.

Later, the B-mode was introduced, utilizing gray scale. By assigning to the returning sound pulses different shades of darkness, depending on their intensities, the varying shades of gray in the image reflected variations in the texture of internal organs.

A significant step in improving ultrasound imaging was the development of the Compounded B-mode. Here the images produced at each probe position are stored until the probe has completed its traverse across the body. At that point all the individual scan images are integrated and displayed as a cross section of the body.

The M-mode basically takes a B-mode image, and records the images over time, so that images from the same part of the body are observed, at different times, for example, to the heart's motion.

Real-time mode allows for visualizing motion of internal structures in a way that is easy to read and understand. It is actually made up of compound B-mode images in frames of about 30 per second.

It is noteworthy that attenuation correction may also be desired for the ultrasound. For example, U.S. Pat. No. 4,389,893, to Ophir, et al., dated Jun. 28, 1983, and entitled, "Precision ultrasound attenuation measurement," whose disclosure is incorporated herein by reference, discloses method and apparatus for measuring an ultrasound attenuation characteristic in a region of interest using ultrasound wherein two statistically independent set of values are accumulated as a difference between logarithms of pairs of each signal set, and the attenuation characteristic calculated as a central tendency parameter of each set of values.

Contrast agents may be used in conjunction with ultrasound imaging, for example as taught by U.S. Pat. No. 6,280,704, to Schutt, et al., entitled, "Ultrasonic imaging system utilizing a long-persistence contrast agent," whose disclosure is incorporated herein by reference.

Magnetic resonance imaging (MRI) is based on the absorption and emission of energy in the radio frequency range of the electromagnetic spectrum, by nuclei having unpaired spins.

The hardware components associated with an MRI imager are:

i. a primary magnet, which produces the $B_o$ field for the imaging procedure;
ii. gradient coils for producing a gradient in $B_o$;
iii. an RF coil, for producing the $B_1$ magnetic field, necessary to rotate the spins by 90° or 180° and for detecting the NRI signal; and
iv. a computer, for controlling the components of the MRI imager.

Generally, the magnet is a large horizontal bore superconducting magnet, which provides a homogeneous magnetic field in an internal region within the magnet. A patient or object to be imaged is usually positioned in the homogeneous field region located in the central air gap for imaging.

A typical gradient coil system comprises an antihelmholtz type of coil. These are two parallel ring shaped coils, around the z axis. Current in each of the two coils flows in opposite directions creating a magnetic field gradient between the two coils.

The RF coil creates a $B_1$ field, which rotates the net magnetization in a pulse sequence. They may be: 1) transmit and receive coils, 2) receive only coils, and 3) transmit only coils.

In this geometry, for in-vivo MRI, the use of catheters equipped with miniature RF coils for internal imaging of body cavities still requires positioning the patient in a conventional large MRI magnet. This environment can result in deficient images because the various orientations of the RF coil, e.g., in an artery, will not be positioned always colinearly with the RF excitation field.

This problem has been resolved by U.S. Pat. No. 5,572,132, to Pulyer, et al., entitled, "MRI probe for external imaging," whose disclosure is incorporated herein by reference, wherein an MRI catheter for endoscopical imaging of tissue of the artery wall, rectum, urinal tract, intestine, esophagus, nasal passages, vagina and other biomedical applications is described.

The invention teaches an MRI spectroscopic probe having an external background magnetic field $B_0$ (as opposed to the internal background magnetic filed of the large horizontal bore superconducting magnet.) The probe comprises (i,j,k) a miniature primary magnet having a longitudinal axis and an external surface extending in the axial direction and (ii) a RF coil surrounding and proximal to the surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

U.S. Pat. No. 6,315,981 to Unger, entitled, Gas filled microspheres as magnetic resonance imaging contrast agents," whose disclosure is incorporated herein by reference, describes the use of gas filled microspheres as contrast agents for magnetic resonance imaging (MRI). Unger further describes how gas can be used in combination with polymer compositions and possibly also with paramagnetic, superparamagnetic, and liquid fluorocarbon compounds as MRI contrast agents. It is further shown how the gas stabilized by polymers would function as an effective susceptibility contrast agent to decrease signal intensity on T2 weighted images; and that such systems are particularly effective for use as gastrointestinal MRI contrast media.

SUMMARY OF THE INVENTION

According to one aspect of the present inveniton, there is provided imaging apparatus, comprising:

a first device, for obtaining a first image, by a first modality, selected from the group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof, wherein the first image is registered to a system of coordinates;

a second device, for obtaining a second, structural image, by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, an intravascular ultrasound, and a combination thereof; and a computerized system, which comprises a registrator for co-registering the second, structural image to the system of coordinates, and an attenuation-instruction generator configured to compute a set of attenuation instructions for the first image, based on the second, structural image.

Additionally, the computerized system is configured to compute, based on the a set of attenuation instructions an attenuation-corrected image of the first image.

Additionally, the computerized system is configured to display a superposition of the attenuation-corrected first image and the second, structural image.

Additionally, the apparatus includes an instrument, registered to the system of coordinates and visible on at least one of the first image and the second, structural image, and wherein the computerized system is further configured to guide the instrument in-vivo, based on the superposition.

Additionally, the registrator for co-registering the second, structural image to the system of coordinates relies on that the first and second devices share a single position-registration device, for co-registering the second, structural image to the system of coordinates.

Alternatively, the registrator for co-registering the second, structural image to the system of coordinates relies on that the first and second devices have substantially equal position-registration devices, for co-registering the second, structural image to the system of coordinates.

Alternatively, the registrator for co-registering the second, structural image to the system of coordinates relies on fiduciary marks visible both on the first image and on the second, structural image, for co-registering the second, structural image to the system of coordinates.

According to another aspect of the present inveniton there is provided imaging apparatus, comprising:

a first detector, for obtaining a first image, by a modality, selected from the group consisting of a gamma scan, a beta scan, and a combination thereof, wherein the first image is registered to a system of coordinates;

a second detector, for obtaining a second, structural image, by a modality, selected from the group consisting of ultrasound, MRI, and a combination thereof; and a computerized system, which comprises a registrator for co-registering the second, structural image to the system of coordinates, and an attenuation-instruction generator configured to compute a set of attenuation instructions for the first image, based on the second, structural image.

Additionally, the imaging apparatus includes an ultrasound transducer operative for focused ablation.

Additionally, the imaging apparatus is designed as a rectum probe.

Alternatively, the imaging apparatus is designed as an endoscope probe.

Additionally, the imaging apparatus is designed to be inserted through a trucar valve.

Alternatively, the imaging apparatus is designed to be mounted on a resectoscope.

Alternatively, the imaging apparatus is designed to be inserted in a catheter.

Alternatively, the imaging apparatus is designed for intravascular imaging.

Alternatively, the imaging apparatus is designed as a handheld, extracorporeal probe.

According to another aspect of the present inveniton, there is provided a rectal probe, comprising:

an intracorporeal portion, which comprises:

a first detector, for obtaining a first image, by a first modality, selected from the group consisting of a gamma scan, a beta scan, and a combination thereof, wherein the first image is registered to a system of coordinates; and a second detector, for obtaining a second, structural image, by a second modality, selected from the group consisting of a ultrasound, MRI, and a combination thereof; and a computerized system, which comprises a registrator for co-registering the second, structural image to the system of coordinates, and an attenuation-instruction generator configured to compute a set of attenuation instructions for the first image, based on the second, structural image.

Additionally, the probe includes movable collimators, operative as vents.

Additionally, the motor further includes motion and position registration in a linear direction into the rectum.

Additionally, the probe includes an ultrasound transducer, adapted for focused ablation.

According to one aspect of the present inveniton, there is provided an imaging method, comprising:

imaging by a first modality, selected from the group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof, wherein the first image is registered to a system of coordinates;

imaging by a second modality, a second device, for obtaining a second, structural image, by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, an intravascular ultrasound, and a combination thereof;

co-registering the second, structural image to the system of coordinates; and computing a set of attenuation instructions for the first image, based on the second, structural image.

Additionally, the method comprises, based on the a set of attenuation instructions, computing an attenuation-corrected first image.

Additionally, the method comprises, displaying an attenuation-corrected first image.

Additionally, the method comprises, superimposing the attenuation-corrected first image and a second, structural image of the second, structural imaging modality.

Additionally, the method comprises, guiding an instrument based on the superposition of the attenuation-corrected first image and the second, structural image.

Additionally, the method comprises, performing focused ablation, based on the superposition of the attenuation-corrected first image and the second, structural image.

According to another aspect of the present inveniton, there is provided a probe, comprising:
- a nuclear-radiation detector of a non-parallel collimation; and
- an ultrasound detector.

Additioally, the non-parallel collimation is a single-collimator collimation.

Alternatively, the non-parallel collimation is a wide-angle collimation.

Alternatively, the non-parallel collimation is a narrow-angle collimation.

Alternatively, the non-parallel collimation is no collimation.

Additionally, the probe is adapted to be handheld.

Alternatively, the probe is adapted for endoscopy.

According to another aspect of the present inveniton, there is provided a probe, comprising:
- a nuclear-radiation detector; and
- an MRI detector, having an external magnetic field.

Additionally, the probe is adapted to be handheld.

Alternatively, the probe is adapted for endoscopy.

According to another aspect of the present inveniton, there is provided a system of intravascular imaging, comprising:
- performing intravascular nuclear-radiation imaging;
- performing intravascular ultrasound; and
- co-registering the nuclear-radiation and the ultrasound images to a system of coordinates.

Additionally, the method includes correcting the nuclear-radiation image for attenuation, based on the ultrasound image.

Additionally, the method includes superimposing the corrected nuclear-radiation image and the ultrasound image.

The present invention successfully addresses the shortcomings of the presently known configurations by providing imaging apparatus, comprising a first device, for obtaining a first image, by a first modality, selected from the group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof, and a second device, for obtaining a second, structural image, by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, an intravascular ultrasound, and a combination thereof, and wherein the apparatus further includes a computerized system, configured to construct an attenuation map, for the first image, based on the second, structural image. Additionally, the computerized system is configured to display an attenuation-corrected first image as well as a superposition of the attenuation-corrected first image and the second, structural image. Furthermore, the apparatus is operative to guide an in-vivo instrument based on the superposition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1H, together, schematically illustrate a first system of combined nuclear-radiation and ultrasound imaging, adapted to provide a correction for radiation attenuation in a tissue, in accordance with a first embodiment of the present invention;

FIGS. 4A-4J schematically illustrate a handheld system for simultaneous nuclear-radiation and ultrasound imaging, in accordance with the present invention;

FIGS. 9A and 9B schematically illustrate ingestible devices for simultaneous nuclear-radiation and ultrasound imaging, in accordance with the present invention;

FIGS. 10A and 10B schematically illustrate a three-dimensional system, for simultaneous nuclear-radiation and ultrasound imaging, in accordance with the present invention;

DESCRIPTION OF THE PREFERRED EMBODIMENTS

Figure 1A:
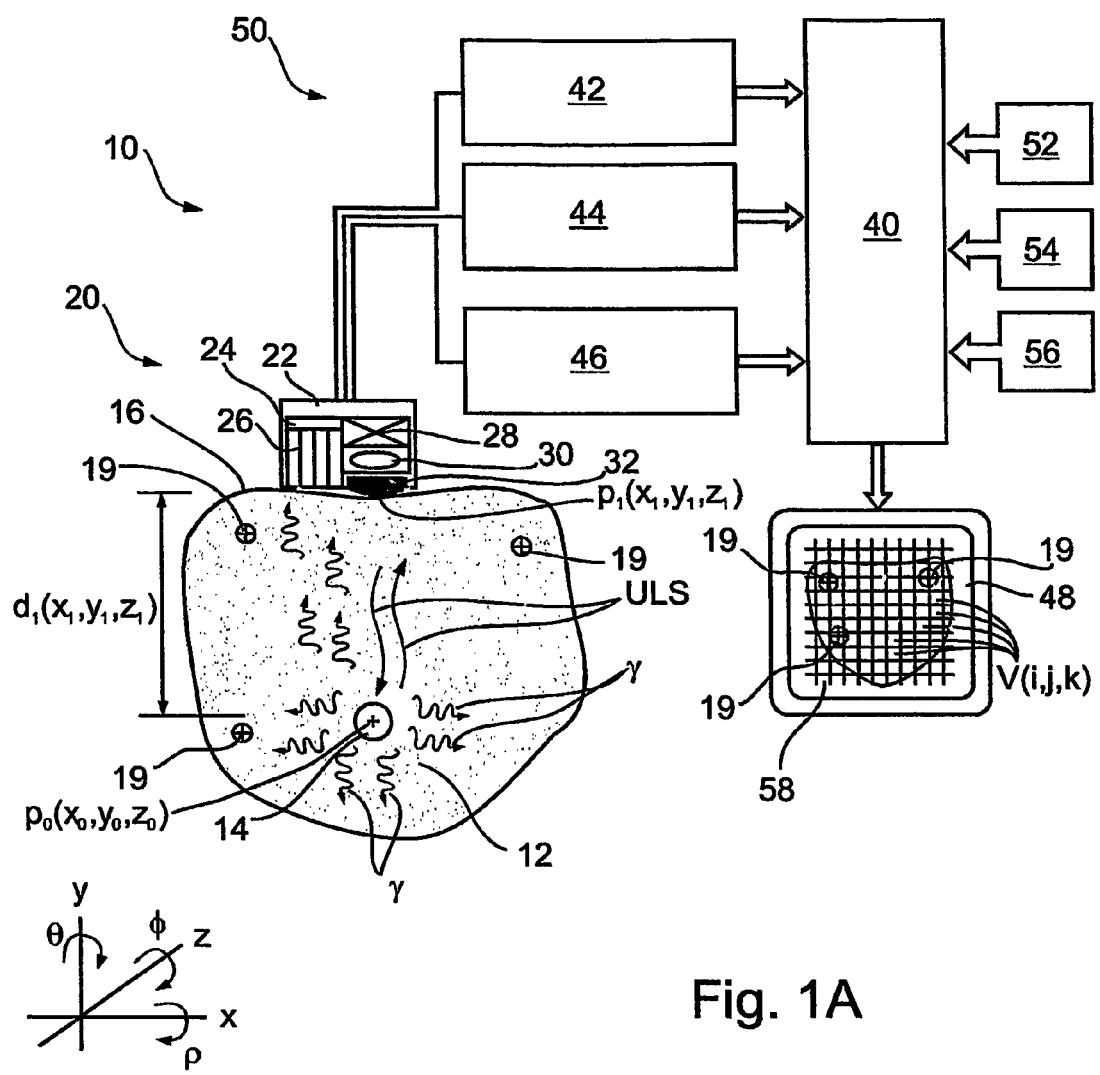

The present invention is of imaging apparatus, comprising a first device, for obtaining a first image, by a first modality, selected from the group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof, and a second device, for obtaining a second, structural image, by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, an intravascular ultrasound, and a combination thereof, and wherein the apparatus further includes a computerized system, configured to construct an attenuation map, for the first image, based on the second, structural image. Additionally, the computerized system is configured to display an attenuation-corrected first image as well as a superposition of the attenuation-corrected first image and the second, structural image. Furthermore, the apparatus is operative to guide an in-vivo instrument based on the superposition.

The principles and operation of the device and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1A-1H, together, schematically illustrate a system 10 of combined nuclear-radiation and ultrasound imaging, adapted to provide a correction for radiation attenuation in a tissue 12, in accordance with a first embodiment of the present invention. System 10 is further adapted to provide an attenuation-corrected nuclear-radiation image and an ultrasound image, wherein the two images may be superimposed, in accordance with the present invention.

As seen in FIG. 1A, system 10 includes a combined nuclear-radiation and ultrasound imaging probe 20, which includes a nuclear-radiation detector 24, having a collimator 26, an ultrasound detector 32, a preferably six-dimensional, position-registering device 30, and related electronic components 28, as known.

Probe 20 is adapted to move across an external surface 16 of tissue 12 and detect any γ radiation, emitted from a source 14. Probe 20 is further adapted to detect ultrasound-ULS which is reflected from source 14.

Tissue 12 preferably includes at least one, and preferably three fiducial marks 19, arranged at different locations along it. Fiducial marks 19 are visible both on the nuclear-radiation image and on the ultrasound image, and are operative to increase the accuracy of the co-registration of the nuclear-radiation and ultrasound images. The fiducial marks may be, for example plastic disks or capsules, filled with a solution of Gd-DTPA. Alternatively, they may be thin lead disks. Alternatively, other fiducial marks, visible both on the nuclear-radiation image and on the ultrasound image may be used. Preferably, three fiducial marks 19 are arranged on different planes.

Additionally, system 10 includes a computer system 50, which includes a nuclear-radiation computer interface 42, associated with nuclear-radiation detector 24, an ultrasound computer interface 44, associated with ultrasound detector 32, and a position-registering computer interface 46, associated with position-registering device 30, wherein interfaces 42, 44, and 46 lead to a computer 40.

Computer 40, which may be a PC, a laptop, or another computer as known, includes nuclear-radiation imaging algorithms 52, ultrasound imaging algorithms 54, and position-registering algorithms 56.

In that sense, using these algorithms, computer system 50 may be considered to include a registrator, for co-registering the ultrasound image and the nuclear-radiation image to a single system of coordinates.

Preferably, computer 40 further includes a display screen 48.

System 10 defines a six-dimensional coordinate system x; y; z; ρ; θ; φ, and a three-dimensional grid 58, which divides tissue 12 into imaginary voxels, where L, M, and N are the total number of voxels in the x, y, and z directions, respectively. Each voxel is denoted as V(i,j,k), as seen on display screen 48.

In accordance with the present invention, system 10 is adapted to provide an attenuation correction to the functional image, obtained with nuclear-radiation detector 24, based on the structural image, obtained with ultrasound detector 32.

The prior art generally relies on x-ray or gamma ray transmission data to provide attenuation correction to gamma nuclear-radiation data. Since x-rays and gamma rays are similar in nature, both being short-wave electromagnetic radiation, they both provide the same type of information, and the approach for obtaining attenuation correction is iterative in nature, requiring heavy computation time. This approach is described, for example, in International Patent Application No. PCT/US90/03722, to Kaplan, SU-1405-819-A, U.S. Pat. No. 5,155,365, to Cann, et al., dated Oct. 13, 1992, U.S. Pat. No. 5,376,795, to Hasegawa, et al., dated Dec. 27, 1994, U.S. Pat. No. 5,210,421, to Gullberg, et al., dated May 11, 1993, U.S. Pat. No. 5,338,936, also to Gullberg, et al., dated Aug. 16, 1994, U.S. Pat. No. 5,559,335, to Zeng and Gullberg, dated Sep. 24, 1996, U.S. Pat. No. 5,672,877, to Liebig, et al., dated Sep. 30, 1997, U.S. Pat. No. 6,310,968, to Hawkins, et al., dated Oct. 30, 2001, U.S. Pat. No. 6,339,652, also to Hawkins, et al., dated Jan. 15, 2002, U.S. Pat. No. 6,384,416, to Turkington, et al., et al, dated May 7, 2002, U.S. Pat. No. 6,429,434, to Watson, et al., dated Aug. 6, 2002, U.S. Pat. No. 6,455,856, to Gagnon, dated, Sep. 24, 2002, and U.S. Pat. No. 6,539,103, to Panin, et al., dated Mar. 25, 2003.

System 10 of the present invention is highly advantageous over the prior art, because it utilizes a structural image of a different nature, for example ultrasound radiation, to provide structural details that are used for attenuation correction of the gamma nuclear-radiation data. The structural details preferably include:

i. the type of a specific tissue layer, for example, soft tissue, cancerous tissue (generally more dense than soft tissue); or bone; and ii. the gamma ray path length in the specific tissue layer.

Ultrasound imaging is uniquely suited for providing this type of information. In ultrasound imaging, high frequency sound waves in the range of 1 to 5 megahertz travel in the body and are reflected by boundaries between different types of tissues. The reflected waves are detected by the ultrasound probe, and the ultrasound instrumentation calculates the distance from the probe to the reflecting boundary, based on the speed of sound in tissue (about 540 m/s) and based on the of travel, which is usually measured in millionths of a second. Additionally, when using gray-scale display, low-level echoes are amplified and recorded together with the higher-level ones, giving many degrees of brightness, so the internal texture of many organs and generally also of cancerous tissue, becomes visible. Thus ultrasound imaging inherently produces the type of information that is needed for attenuation correction.

Figure 1B:
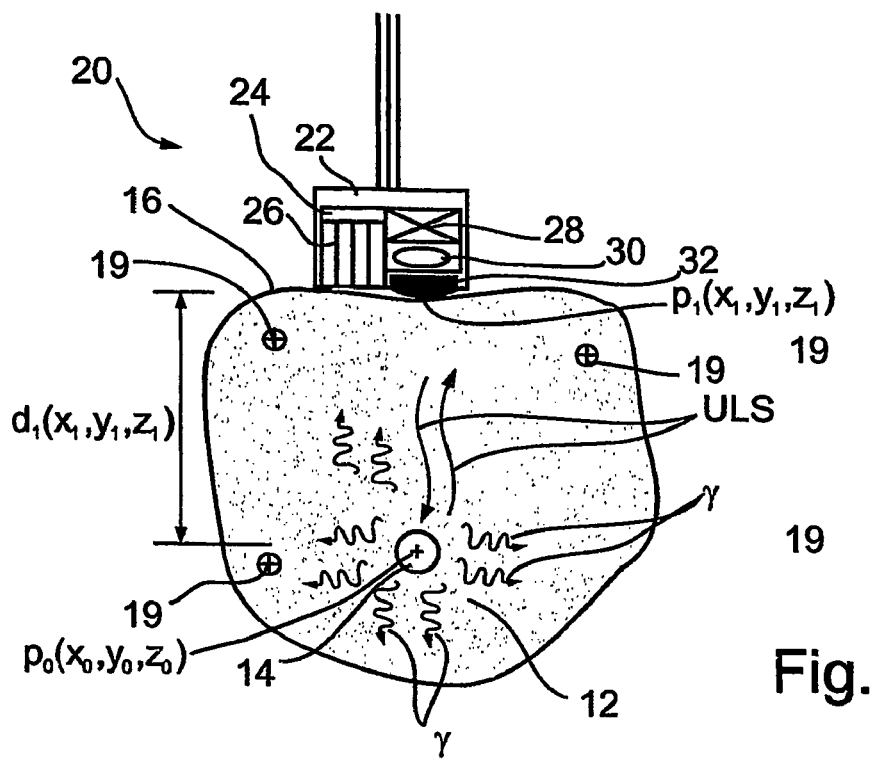
Figure 1C:
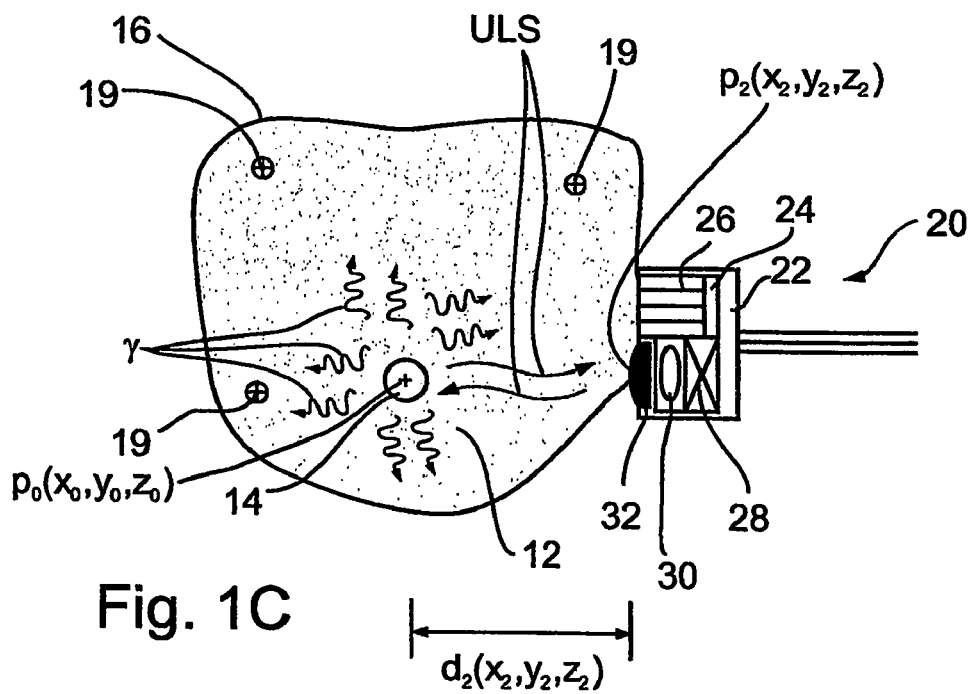
Figure 1D:
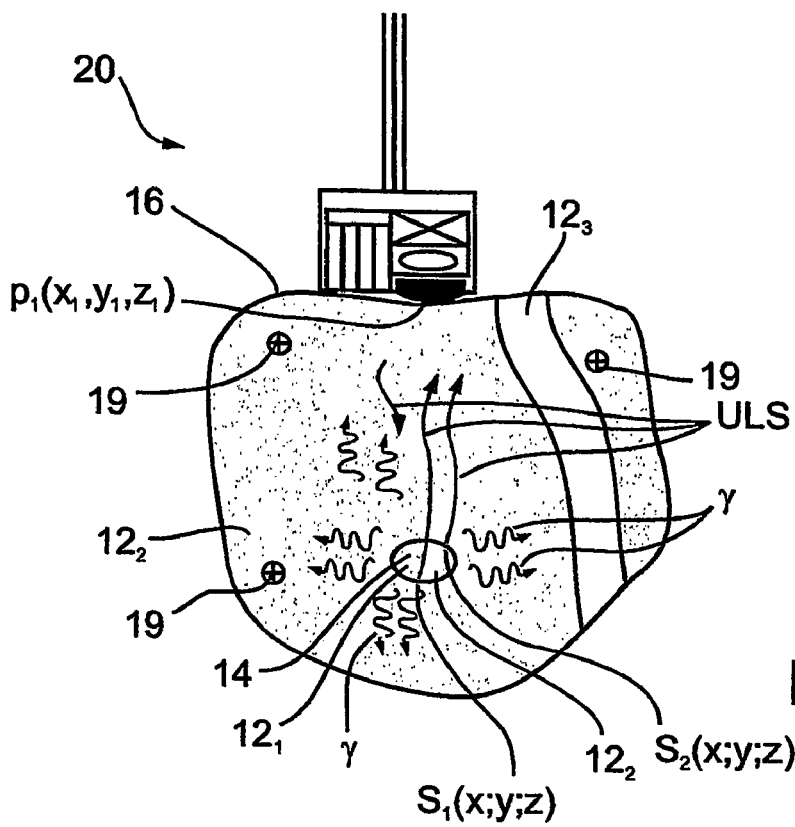
Figure 1E:
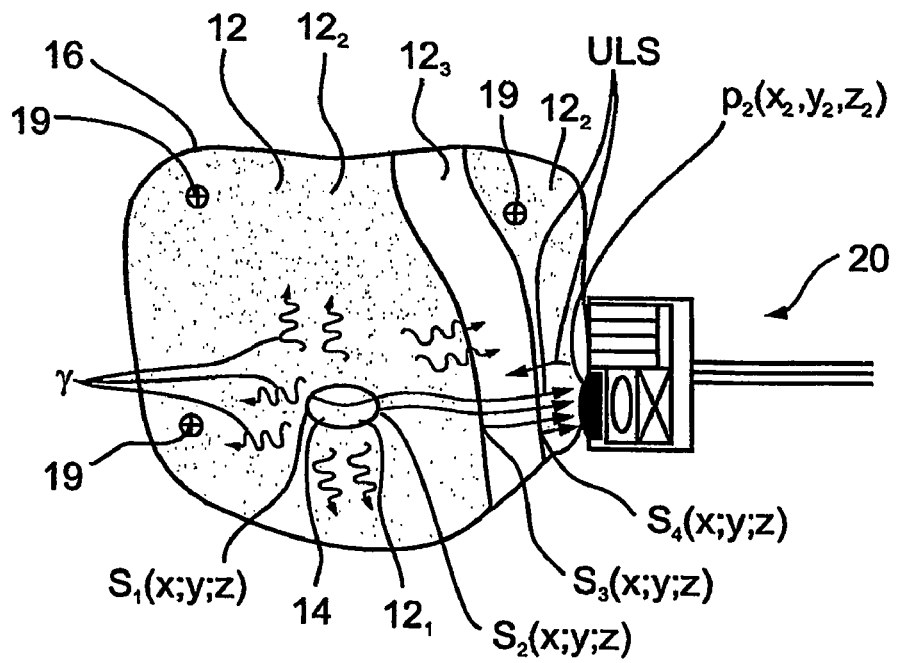

The method of providing a correction for radiation attenuation in tissue 12, in accordance with the present invention, is described in conjunction with FIGS. 1B-1C, for a homogenous tissue, and in conjunction with FIGS. 1D-1G, for a tissue made up of several layers of different densities and attenuation characteristics.

As seen in FIGS. 1B-1C, for homogenous tissue 12, as probe 20 moves across external surface 16, it detects γ radiation, emitted from substantially point source 14. Defining:

i. $P_0(x_0;y_0;z_0)$ as the position of substantially point source 14;

ii. $P_1(x_1;y_1;z_1)$ as the position of probe 20 in FIG. 1B, at a distance $d_1(x_1;y_1;z_1)$ from point source 14; and iii. $P_2(x_2;y_2;z_2)$ as the position of probe 20 in FIG. 1C, at a distance $d_2(x_2;y_2;z_2)$ from point source 14; and iv. $d_p(x_p;y_p;z_p)$ as a general position of probe 20, at a distance $d_p(x_p;y_p;z_p)$ from point source 14, It will be appreciated that the path length that the gamma rays make, from substantially point source 14 to the position of probe 20 is different for each probe position. Thus, the extent of attenuation, which the gamma rays encounter is different for each probe position, and a different attenuation correction needs to be applied, for each case.

In a homogenous tissue, the transmitted intensity $I_p(E)$ of a monochromatic gamma ray beam of a photon energy E, an initial intensity $I_0$, and a path length $d_p(x_p;y_p;z_p)$, is a function of the photon energy E, path length $d_p(x_p;y_p;z_p)$, and an energy-dependent total linear attenuation coefficient, $\mu_{total}(E)$. The total linear attenuation coefficient, $\mu_{total}(E)$, accounts for the total interactions of emitted photons of energy E with the tissue, through photoelectric absorption, Compton scattering, and pair production. This relationship is described by Equation 1:

$$I_p(E)=I_0(E)\exp[-\mu_{total}(E)\cdot d_p(x_p;y_p;z_p)] \quad [1]$$

The total linear attenuation coefficient $\mu_{total}(E)$ is expressed in $cm^{-1}$ and is obtained by multiplying the total tissue cross section, in $cm^2/gr$ by the tissue density, in $gr/cm^3$.

A widely used method for obtaining an attenuation correction is Chang's method, which applies to situations of uniform attenuation throughout the tissue. An energy-dependent attenuation correction coefficient $C_p(E)$ may be obtained for each probe 20 position $P_p(x_p; y_p; z_p)$, from Equation 2:

$$C_p(E)=\{\exp[\mu_{total}(E)]\cdot d_p(x_p;y_p;z_p)\}^{-1} \quad [2]$$

In accordance with the present invention, the path length that the gamma rays make $d_p(x_p;y_p;z_p)$, for each imaging position $d_p(x_p;y_p;z_p)$ may be obtained from the ultrasound image, while values of $\mu_{total}(E)$ for different tissue types are generally known. Thus, $C_p(E)$ for each probe position may be caluculated.

The correction factor, $C_p(E)$, is a multiplication factor. For obtaining a corrected nuclear-radiation image, the gamma counts at each probe position $d_p(x_p;y_p;z_p)$ are multiplied by the correction factor, $C_p(E)$ which corresponds to that energy and that position. A corrected nuclear-radiation image may thus be produced.

In a sense, the collection of $C_p(E)$ for each position $d_p(x_p;y_p;z_p)$ of nuclear radiation detector 24, as calculated by Equaiton 2, may be defined as a set of attenuation instructions, for homogenous tissue.

Computer system 50 is configured to compute the set of attenuation instructions. In that sense, computer system 50 may be considered to include an attenuation-instruction generator, configured to compute the set of attenuation instructions.

Additionally, computer system 50 is configured to compute an attenuation-corrected nuclear-radiation image, based on the set of attenuation instructions.

Furthermore, computer system 50 is configured to display the attenuation-corrected nuclear-radiation image.

Additionally, computer system 50 is configured to display a superposition of the attenuation-corrected nuclear-radiation image, and the ultrasound image.

FIGS. 1D-1G illustrate a more complex situation, where several tissue layers of different densities and attenuation characteristics are involved. For example, tissue $12_1$ may be a cancerous tissue, tissue $12_2$ may be a soft tissue, and tissue $12_3$ may be a bone tissue. The different layers are bounded by different surfaces, such as $S_1(x;y;z)$, $S_2(x;y;z)$, $S_3(x;y;z)$, $S_4(x;y;z)$, and external surface 16, and these are operative as reflective boundaries for ultrasound radiation. The tissue type and thickness of each layer may be determined by the ultrasound image, Based on the structural details obtained from the ultrasound image, a three-dimensional gamma attenuation map may be constructed. Tissue 12 is divided into voxels $V(i,j,k)$, small enough so that each is assigned one tissue type, and its corresponding total linear attenuation coefficient, $\mu_{total}(E)$.

FIG. 1F illustrates an example of a single-voxel layer of a three-dimensional gamma attenuation map, wherein in the present example, one voxel is assigned tissue type $12_1$, with a corresponding total linear attenuation coefficient, $\mu_{total}(E)_1$ some voxels are assigned tissue type $12_2$, with corresponding total linear attenuation coefficient, $\mu_{total}(E)_2$, and the remainder are assigned tissue type $12_3$, with corresponding total linear attenuation coefficient, $\mu_{total}(E)_3$. It will be appreciated that in practice, the three-dimensional gamma attenuation map includes a plurality of voxel layers, where L, M, and N are the total number of voxels in the x, y, and z directions respectively.

As seen in FIG. 1G, a gamma path length in each voxel $V(i,j,k)$ may be defined as $r(i,j,k)$, wherein the total path length $d(x;y;z)$ may be described by Equation 3:

$$d_p(x_p; y_p; z_p) = \sum_{i=1}^{L}\sum_{j=1}^{M}\sum_{k=1}^{N} r_p(i,j,k) \quad [3]$$

An attenuation correction coefficient for each voxel, $C(i,j,k)$, based on the total linear attenuation coefficient of that voxel, $[\mu_{total}(E)](i,j,k)$ and the path length within that voxel $r(i,j,k)$, may be obtained for each probe 20 position $P_p(x_p;y_p;z_p)$ from Equation 4:

$$C_p(E) = \frac{1}{L}\cdot\frac{1}{M}\cdot\frac{1}{N}\sum_{k=1}^{L}\sum_{j=1}^{M}\sum_{i=1}^{N}\{\exp\text{-}[\mu_{total}(E)](i,j,k)\cdot r_p(i,j,k)\}^{-1} \quad [4]$$

As before, the gamma counts at each probe position $P_p(x_p;y_p;z_p)$ are multiplied by the correction factor, $C_p(E)$ which corresponds to that energy and that position. A corrected nuclear-radiation image may thus be produced.

Again, the collection of $C_p(E)$ for each position $P_p(x_p;y_p;z_p)$ of nuclear radiation detector 24, as calculated by Equaiton 4, may be defined as a set of attenuation instructions, for non-homogenous tissue.

Computer system 50 is configured to compute the set of attenuation instructions, as well as an attenuation-corrected nuclear-radiation image, based on the set of attenuation instructions, and to display the attenuation-corrected nuclear-radiation image, possibly also, superimposed with the ultrasound image.

In that sense, computer system 50 may be considered to include an attenuation-instruction generator, configured to compute the set of attenuation instructions.

It will be appreciated that system 10 may also include a set of algorithms that predicts the location of source 14 and an uncertainty region, based on a system measurement error, from the measurements. These algorithms may be used to guide an operator (not shown) to perform additional measurements so as to minimize the uncertainty region.

In accordance with a preferred embodiment of the present invention, system 10 is adapted to display a superposition of an attenuation-corrected functional image and a structural image, for example on display screen 48. The superimposed image may be provided as a series of two-dimensional slices, or as a three-dimensional perspective view, which preferably may be rotated. The advantages of this superposition are described in detail in commonly owned parent U.S. application Ser. No. 10/343,792, whose disclosure is incorporated herein by reference.

Additionally, as taught in commonly owned U.S. Pat. No. 6,567,687, to Front, et al., dated May 20, 2003, and entitled, "Method and system for guiding a diagnostic or therapeutic instrument towards a target region inside the patient's body," whose disclosure is incorporated herein by reference, system 10 may be adapted for guiding an instrument to the body, based on the superposition of an attenuation-corrected functional image, and a structural image.

Thus, as seen in FIG. 1H, an instrument having a tip 25, which is visible on at least one of the nuclear-radiation image and on the ultrasound image and preferably on both, may be guided to a target, such as source 14, based on the superposition of the attenuation-corrected nuclear-radiation image and the ultrasound image, for example on display screen 48: Tip 25 may be, for example, a biopsy needle, a laser diode, an optical fiber, a cryosurgery device, a knive edge, an electrostimulation device, or a medication-dispensing device, or a combination of the above.

Nuclear-radiation detector 24 may be a solid-state or a scintillation detector, as known, and may be a single-pixel detector, or a pixilated detector module. For example, nuclear-radiation detector 24 may be a single module array, of 4×4, or of 16×16 pixels, formed of room temperature CdZnTe, obtained from IMARAD IMAGING SYSTEMS LTD., of Rehovot, ISRAEL, 76124, www.imarad.com. Preferably, nuclear-radiation detector 24 is connected to a preamplifier (not shown).

Collimator 26 may be, for example, a single tube collimator, a grid of parallel collimators, a wide-angle collimator, or a narrow-angle collimator, as known.

Electronic components 28 may include a dedicated control circuitry, a processor, an Application Specific Integrated Circuit (ASIC), or a microcomputer, as known, and may further include built-in intelligence. A memory unit may be integrated with it.

Position-registering device 30 may be a navigation sensor, preferably, for registration of six coordinates x;y;z axes and rotational angles ρ, θ and φ. It may be, For example, a magnetic tracking and location system, as known, for example, miniBIRD®, commercially available from Ascension Technology Corporation, P.O. Box 527, Burlington, Vt. 05402 USA (web page www Dot ascensiontech dot com/graphic Dot htm).

Alternatively, position-registering device 30 may be a miniature global positioning system (GPS), as known, for example, a miniature GPS of Zarlink Semiconductor Inc., 400 March Road, Ottawa, Canada K2K 3H4, Phone 613 592-0200, Fax: 613 591-2317, Email: corporate at zarlink Dot com, Web: www Dot zarlink Dot com.

Alternatively, position-registering device 30 may be an articulated arm, which serves as a position tracking system, as taught in commonly owned, parent application Ser. No. 10/343,792, whose disclosure is incorporated herein by reference, in conjunction with FIG. 2 therein.

Alternatively, position-registering device 30 may be, for example, a pair of three coaxially aligned accelerometers, which serves as a position tracking system, as taught in parent application Ser. No. 10/343,792, in conjunction with FIG. 3 therein.

Alternatively, a potentiometer based position tracking system, a sound wave based position tracking system, a radio frequency based position tracking system, an optical based position tracking system, or a gantry, as known, may be used. Alternatively, any other positioning registering device may be used. It will be appreciated that position-registering device 30 may be only a 3-D positioning registering device, for registration of three coordinates x;y;z.

Ultrasound detector 32 may be formed of array transducers so as to have the ability to be steered as well as focused, as known. Additionally, ultrasound detector 32 is preferably adapted for gray-scale display, as known.

Figure 2A:
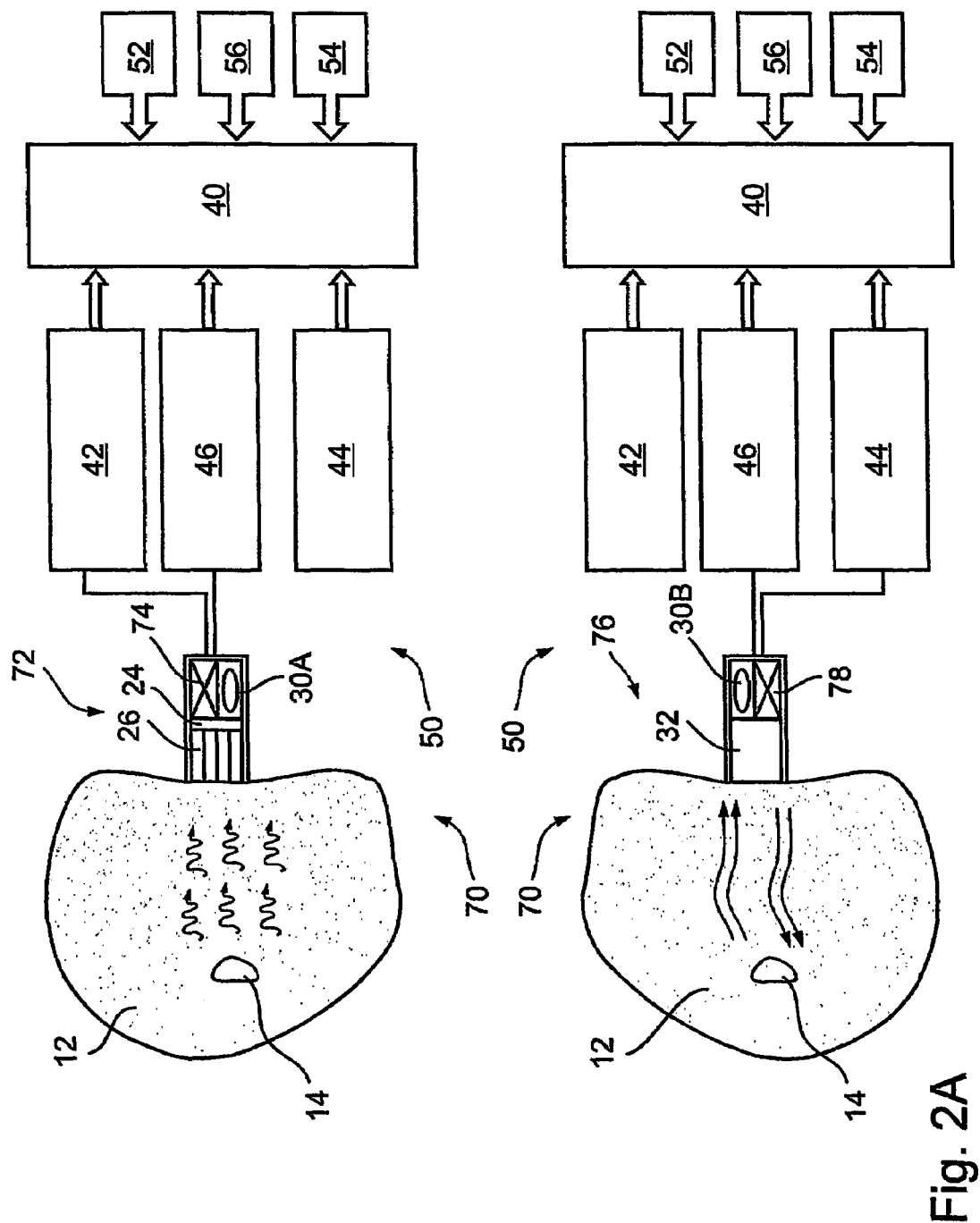
FIGS. 2A and 2B schematically illustrates other systems of combined nuclear-radiation and ultrasound imaging, adapted to provide a correction for radiation attenuation in a tissue, in accordance with alternative embodiments of the present invention.
Figure 2B:
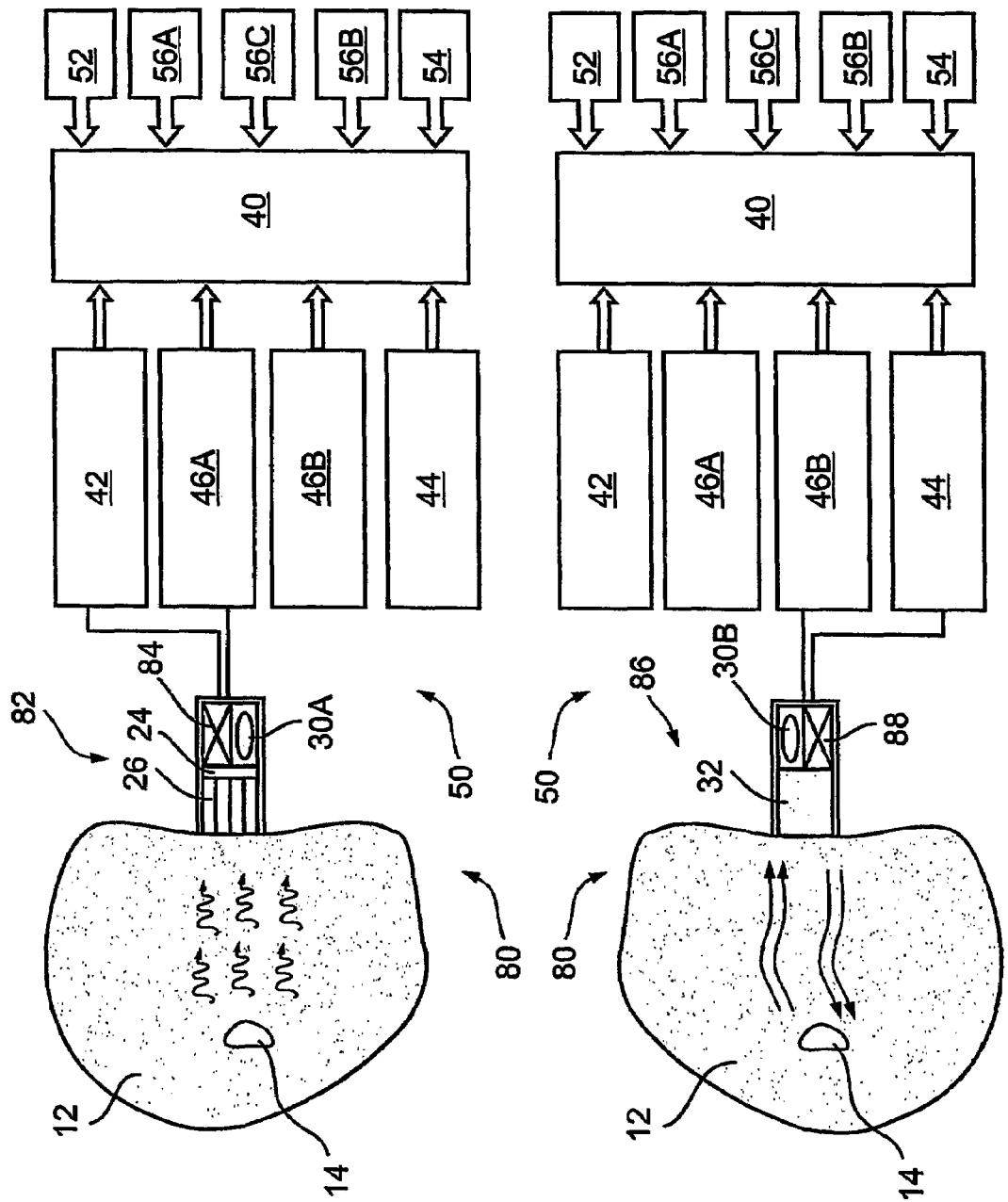

Referring further to the drawings, FIGS. 2A and 2B schematically illustrate other systems of combined nuclear-radiation and ultrasound imaging, adapted to provide a correction for radiation attenuation in tissue 12, in accordance with alternative embodiments of the present invention. The other systems are further adapted to provide an attenuation-corrected nuclear-radiation image and an ultrasound image, wherein the two images may be superimposed, in accordance with the present invention.

FIG. 2A describes a system 70, which is analogous to system 10 hereinabove, but includes two separate probes as follows:

i. a nuclear-radiation probe 72, which includes nuclear-radiation detector 24, having collimator 26, a preferably six-dimensional, position-registering device 30A, and related electronic components 74, as known; and ii. an ultrasound probe 76, which includes ultrasound detector 32, a preferably six-dimensional, position-registering device 30B, and related electronic components 78, as known.

System 70 includes computer system 50, which includes nuclear-radiation computer interface 42, associated with nuclear-radiation detector 24, ultrasound computer interface 44, associated with ultrasound detector 32, and position-registering computer interface 46, associated with the two position-registering devices 30A and 30B, wherein interfaces 42, 44, and 46 lead to computer 40.

In that sense, using these algorithms, computer system 50 may be considered to include a registrator, for co-registering the ultrasound image and the nuclear-radiation image to a single system of coordinates.

The operation and capabilities of system 70 are analogous to those of system 10 of FIG. 1A-1H hereinabove, but in place of the single imaging process when using probe 20 hereinabove, separate nuclear-radiation imaging and ultrasound imaging are performed.

Preferably, tissue 12 includes at least three fiducial marks 19, operative to increase the accuracy of position co-registration of the nuclear-radiation and ultrasound images.

In accordance with a preferred embodiment of the present invention, position-registering devices 30A and 30B are identical units. Alternatively, a removable unit may be used interchangeably, as position-registering device 30A and as position-registering device 30B.

FIG. 2B describes a system 80, Which is analogous to system 10 hereinabove, but includes two separate probes, and two different position-registering devices as follows:

i. a nuclear-radiation probe 82, which includes nuclear-radiation detector 24, having collimator 26, preferably, six-dimensional, position-registering device 30A, and related electronic components 84, as known; and ii. an ultrasound probe 86, which includes ultrasound detector 32, preferably, six-dimensional, position-registering device 30B, and related electronic components 88, as known.

System 80 includes computer system 50, which includes nuclear-radiation computer interface 42, associated with nuclear-radiation detector 24, ultrasound computer interface 44, associated with ultrasound detector 32, and position-registering computer interfaces 46A and 46B, associated with the two position-registering devices 30A and 30B, wherein interfaces 42, 44, 46A and 46B lead to computer 40. Additionally, computer 40 includes position-registering algorithms 56A and 56B and co-registration algorithms 56C for co-registering input of the two different position-registering devices, based on at least three fiducial marks 19.

In that sense, using these algorithms, computer system 50 may be considered to include a registrator, for co-registering the ultrasound image and the nuclear-radiation image to a single system of coordinates.

Co-registration of this type is taught, for example, in commonly owned U.S. patent application Ser. No. 10/616,307, to Kimchy et al., entitled, "Radioactive emission detector equipped with a position tracking system."

The operation and capabilities of systems 80 are analogous to those of systems 10 (FIG. 1A-1H) and 70 (FIG. 2A) hereinabove, but position-registering devices 30A and 30B are different types of units, and each has its own position-registering computer interface. For example, position-registering device 30A may be a miniBIRD® and position-registering device 30B may be an articulated arm.

Preferably, tissue 12 includes at least three fiducial marks 19, operative to increase the accuracy of position co-registration of the nuclear-radiation and ultrasound images.

Thus, computer 40 includes position-registering algorithms 56A and 56B and co-registration algorithms 56C for co-registering input of the two different position-registering devices, based on the at least three fiducial marks 19.

In accordance with another embodiment of the present invention, the nuclear-radiation probe may be a three-dimensional system such as SPECT or PET, and the ultrasound probe may be a three-dimensional ultrasound system.

The associated gantries of the nuclear-radiation system, on the one hand, and of the three-dimensional ultrasound, on the other, are operative as position registering devices 30A and 30B, each having it own computer interface, 46A and 46B, respectively, as described in FIG. 2B.

Figure 3:
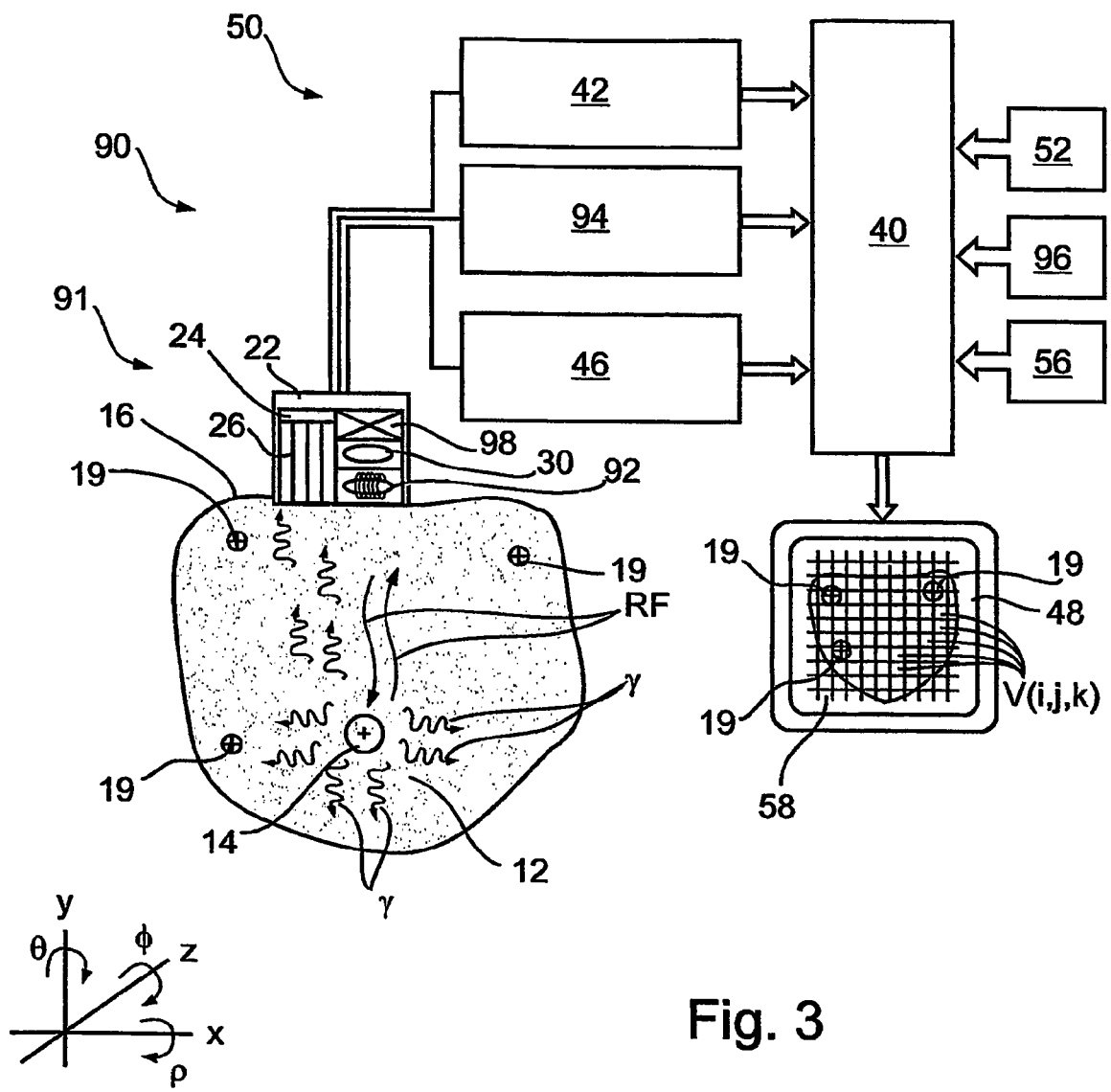
FIG. 3 schematically illustrates a system of combined nuclear-radiation and MRI, adapted to provide a correction for radiation attenuation in a tissue, in accordance with another embodiment of the present invention.

Referring further to the drawings, FIG. 3 schematically illustrates a system 90 of combined nuclear-radiation and magnetic resonance imaging (MRI), adapted to provide a correction for radiation attenuation in a tissue, in accordance with another embodiment of the present invention. System 90 is further adapted to provide an attenuation-corrected nuclear-radiation image and a magnetic resonance image, wherein the two images may be superimposed, in accordance with the present invention.

The present embodiment follows the teachings of U.S. Pat. No. 5,572,132, to Pulyer, et al., entitled, "MRI probe for external imaging," whose disclosure is incorporated herein by reference, wherein an MRI catheter for endoscopical imaging of tissue of the artery wall, rectum, urinal tract, intestine, esophagus, nasal passages, vagina and other biomedical applications is described.

U.S. Pat. No. 5,572,132 teaches an MRI spectroscopic probe having an external background magnetic field $B_0$ (as opposed to the internal background magnetic filed of the large horizontal bore superconducting magnet.) The probe comprises (i,j,k) a miniature primary magnet having a longitudinal axis and an external surface extending in the axial direction and (ii) a RF coil surrounding and proximal to the surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

As seen in FIG. 3, system 90 includes a combined nuclear-radiation and magnetic resonance imaging probe 91, which includes nuclear-radiation detector 24, having collimator 26, an MRI probe 92, preferably, six-dimensional, position-registering device 30, and related electronic components 98, as known.

Combined imaging probe 91 is adapted to move across an external surface 16 of tissue 12 and detect any γ radiation. emitted from a source 14. Probe 20 is further adapted to detect RF of excited nuclei in tissue 12.

Tissue 12 preferably includes at least one, and preferably three fiducial marks 19, arranged at different locations along it. Fiducial marks 19 are visible both on the nuclear-radiation image and on the magnetic resonance image, and are operative to increase the accuracy of the co-registration of the nuclear-radiation and magnetic resonance images. The fiducial marks may be, for example plastic disks or capsules, filled with a solution of Gd-DTPA, for the nuclear radiation, and filled with some paramagnetic, superparamagnetic, or liquid fluorocarbon compounds, for MRI, preferably, in different compartments. Preferably, three fiducial marks 19 are arranged on different planes.

Additionally, system 90 includes computer system 50, which includes nuclear-radiation computer interface 42, associated with nuclear-radiation detector 24, an MRI computer interface 94, associated with MRI probe 92, and position-registering computer interface 46, associated with position-registering device 30, wherein interfaces 42, 94, and 46 lead to computer 40.

In that sense, using these algorithms, computer system 50 may be considered to include a registrator, for co-registering the magnetic resonance image and the nuclear-radiation image to a single system of coordinates.

Thus, the MRI may provide structural details for the construction of a three-dimensional gamma attenuation map.

It will be appreciated that separate probes, in a manner analogous to that described in FIGS. 2A and 2B are similarly possible.

In accordance with another embodiment of the present invention, the nuclear-radiation probe may be a three-dimensional system such as SPECT or PET, and the magnetic resonance system is a conventional three-dimensional system, having a large horizontal bore superconducting magnet, which provides a homogeneous magnetic field in an internal region within the magnet, wherein the patient is positioned in the homogeneous field region located in the central air gap for imaging.

The associated gantries of the nuclear-radiation system, on the one hand, and of the MRI, on the other, are operative as position registering devices 30A and 30B, each having it own computer interface, 46A and 46B, respectively. This situation is analogous to that described in FIG. 2B, hereinabove.

Thus, in accordance with the present invention, the imaging probe or probes may be designed for extracorporeal imaging, as two three-dimensional systems, each positioned on its gantry. Alternatively, a single gantry may be used for both.

Alternatively, the imaging probe or probes may be hand-held, adapted for free-hand movement.

In accordance with the present invention, ablation by ultrasound may be provided, for example, for focused ablation of a cancerous tissue. In accordance with a first embodiment, ultrasound detector 32 (FIG. 1A) is adapted for ablation. Alternatively, another ultrasound transducer is used for the ablation.

In accordance with the present invention, attenuation correction may be applied to any one of the following modalities: a gamma scan, a beta scan, x-rays, SPECT, PET, CT, and a combination thereof. Additionally, the attenuation correction may be based on a structural image, obtained by any of the following modalities: a two-dimensional ultrasound, a three-dimensional ultrasound, MRI operative by an external magnetic field, MRI operative by an internal magnetic field, and a combination thereof.

In accordance with the present invention, the method of imaging includes:

i. imaging by a first modality, selected from the group consisting of SPECT, PET, CT, an extracorporeal gamma scan, an extracorporeal beta scan, x-rays, an intracorporeal gamma scan, an intracorporeal beta scan, and a combination thereof, registered to a system of coordinates;

ii. imaging by a second modality, selected from the group consisting of a three-dimensional ultrasound, an MRI operative by an internal magnetic field, an extracorporeal ultrasound, an extracorporeal MRI operative by an external magnetic field, an intracorporeal ultrasound, an intracorporeal MRI operative by an external magnetic field, and a combination thereof;

iii. co-registering the imaging by the second modality to the system of coordinates; and iv. constructing an attenuation map, for the first modality, based on the second, structural modality.

EXAMPLES

Reference is now made to the following examples, which together with the above descriptions, illustrate the invention in a non-limiting fashion.

Example 1

Referring further to the drawings, FIGS. 4A-4E schematically illustrate a handheld system 100 for simultaneous nuclear-radiation and ultrasound imaging, in accordance with the present invention, as taught in conjunction with FIG. 1A, hereinabove.

Handheld system 100 is adapted to perform freehand, extracorporeal scanning by nuclear radiation and ultrasound, simultaneously. Additionally, computer system 50 (FIG. 1A) is adapted to receive input from handheld system 100 and provide an attenuation-corrected nuclear-radiation image as well as a superposition of the attenuation-corrected nuclear-radiation image and the ultrasound image, for example, on display screen 48. Furthermore, handheld system 100 may be operative to guide an in-vivo instrument tip 25 (FIG. 1H) based on the superposition of the attenuation-corrected nuclear-radiation image and the ultrasound image, for example, as seen on display screen 48 (FIG. 1H).

Figure 4A:
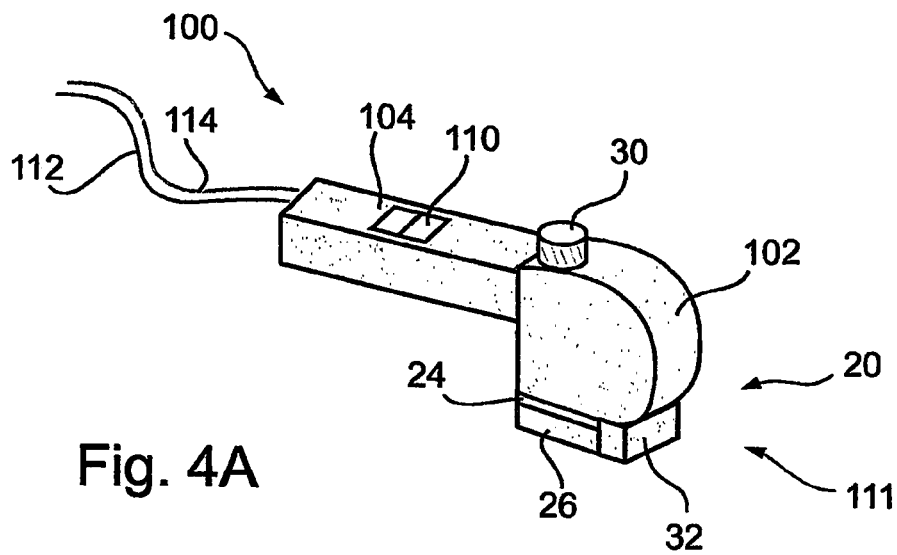

As seen in FIG. 4A, handheld system 100 preferably includes a housing 102, wherein various electronic components 28 (FIG. 1A) are contained. Housing 102 is preferably formed of a rigid, lightweight plastic, a composite, or the like, and includes a handle 104, for easy maneuvering. Handheld system 100 defines a proximal ends 111 with respect to the tissue.

Handheld system 100 further includes combined nuclear-radiation and ultrasound imaging probe 20, having nuclear-radiation detector 24, preferably also, collimator 26, ultrasound detector 32, and preferably six-dimensional, position-registering device 30.

Handheld system 100 further includes a control unit 110, for example for activating and deactivating handheld system 100. Control unit 110, which may be mounted on housing 102, may include basic control knobs, such as "stop", "start", and "pause." Preferably, control unit 110 is adapted to operate nuclear-radiation imaging, alone, ultrasound imaging, alone, and nuclear-radiation and ultrasound imaging, simultaneously.

A cable 112 may be used to provide power communication between handheld system 100 and the grid (not shown), or between handheld system 100 and computer system 50 (FIG. 1A)

Additionally, a cable 114 may be used to provide signal communication between handheld system 100 and computer system 50 (FIG. 1A), leading to nuclear-radiation computer interface 42, ultrasound computer interface 44, and position-registering computer interface 46, wherein interfaces 42, 44, and 46 lead to computer 40.

Figure 4B:
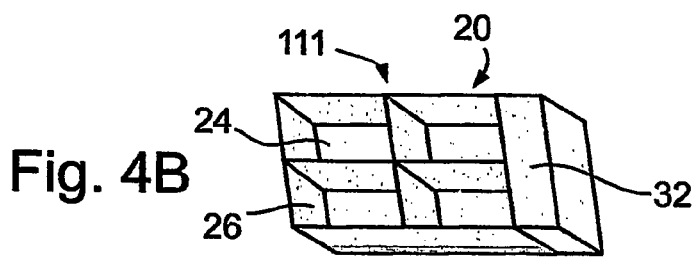

As seen in FIG. 4B, collimator 26 may be a parallel grid collimator, for example, of 4×4, or of 16×16 cells. Alternatively, collimator 26 may be a single tube wide-bore collimator, a wide-angle collimator, a narrow-angle collimator, or another collimator, as known. A plurality of tube collimators may also be used. Alternatively, no collimator is used. Collimator 26, may be formed for example, of lead or of tungsten, and have a length of about 10 to 30 mm, and preferably, about 15 mm, and a width parameter or a diameter of about 10 mm. It will be appreciated that other dimensions, which may be larger or smaller, are also possible.

Nuclear radiation detector 24 may be, for example, a single module array, for example, of 4×4, or of 16×16 pixels, of room temperature CdZnTe, having a width of about 10 mm and a thickness of about 5 mm, and obtained, from IMARAD IMAGING SYSTEMS LTD., of Rehovot, ISRAEL, 76124, www.imarad.com.

Ultrasound detector 32 may be formed of array transducers so as to have the ability to be steered as well as focused, as known. Additionally, ultrasound detector 32 is preferably adapted for gray-scale display, as known.

Additionally, as seen in FIG. 4B since it is preferred that ultrasound detector 32 forms contact with the tissue, ultrasound detector 32 is aligned with proximal edge 111 of collimator 26, so as to press against the tissue, when scanning.

Figure 4C:
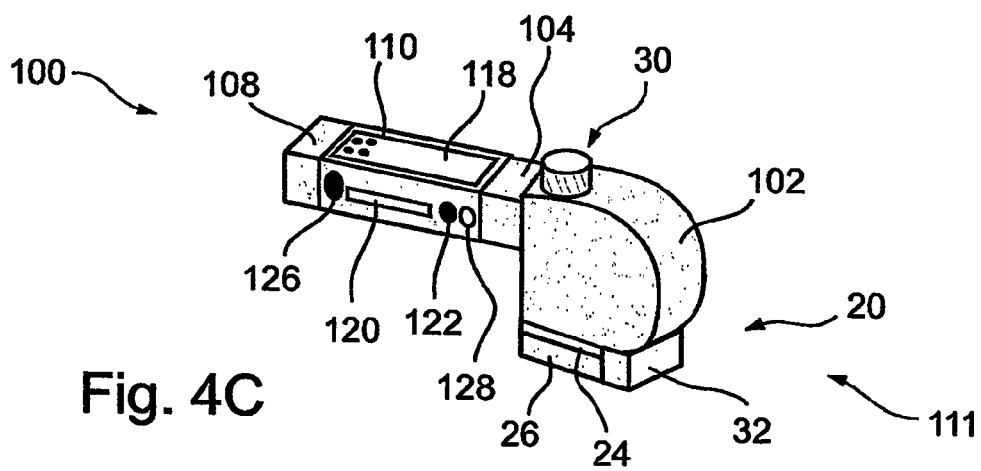

An alternative embodiment of system 100 is illustrated in FIG. 4C. Control unit 110 may be any one of a dedicated control circuitry, a processor, an ASIC, or a microcomputer, as known, and may further include a memory unit, integrated with it. Additionally, control unit 110 may include a display screen 118, mounted on housing unit 102, for displaying information such as gamma counts, gamma energies, ultrasound reflections, probe 20 position, and the like. Display screen 118 may be interactive, for control and display. Control unit 110 may further include a data unit 120, for receiving a diskette, a minidisk, or the like. Preferably, data unit 120 is a read and write unit. An eject button 122 may be included with data unit 120.

A preferably rechargeable power source 108 may provide power to handheld system 100 and a transceiver 126, operating by RF, or IR, may be used to provide wireless communication with computer system 50, for example, using the Blue-Tooth protocol. It will be appreciated that a separate receiver and a separate transmitter may be used. Accordingly, cables 112 and 114 (FIG. 4A) need not be used with the present embodiment, during operation. However, cable 112 may be used for recharging handheld system 100 and cable 114 may be used for downloading information from handheld system 100 to computer system 50, when desired.

Additionally, a signal connector 128, for example, a UBS connector 128 may be provided.

In accordance with the present invention, ultrasound detector 32 is further adapted for focused ablation.

It will be appreciated that combined probe 91 (FIG. 3) for nuclear-radiation imaging and MRI may be used, in place of, or in addition to probe 20, as taught in conjunction with FIG. 3.

Figure 4D:
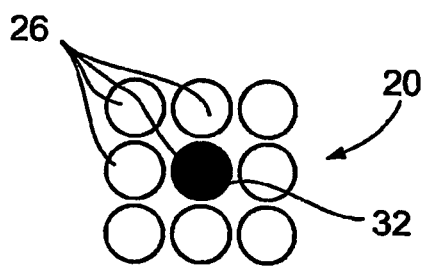
Figure 4E:
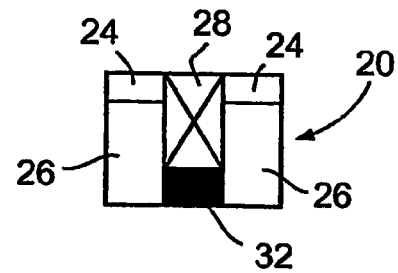

An alternative embodiment of system 100 is illustrated in FIGS. 4D and 4E, showing proximal view with respect to the tissue and side view, respectively. Accordingly, Collimator 26 is arranged as a plurality of tubes, and ultrasound detector 32 is positioned at their center.

Example 2

Referring further to the drawings, FIGS. 4F-4J schematically illustrate a handheld system 140 for simultaneous nuclear-radiation and ultrasound imaging, in accordance with the present invention, as taught in conjunction with FIG. 2A, hereinabove.

System 140 is analogous to system 70 of FIG. 2A. Thus, two separate handheld probes: probe 72 for nuclear radiation imaging and probe 76 for ultrasound are used, both having substantially identical position registering devices 30A and 30B. The manner of using system 140 is similar to that of using system 100, however, in place of simultaneous scanning, for nuclear radiation and ultrasound, each is performed individually, and computer system 50 combines the results.

Thus, handheld system 140 is adapted to perform freehand, extracorporeal scanning by nuclear radiation and ultrasound. Additionally, computer system 50 (FIG. 2A) is adapted to receive input from handheld system 140 and provide an attenuation-corrected nuclear-radiation image as well as a superposition of the attenuation-corrected nuclear-radiation image and the ultrasound image, for example, on display screen 48. Furthermore, handheld system 140 may be operative to guide an in-vivo instrument tip 25 (FIG. 1H) based on the superposition of the attenuation-corrected nuclear-radiation image and the ultrasound image, for example, as seen on display screen 48 (FIG. 1H).

As seen in FIG. 4G, collimator 26 may be a single tube collimator. Alternatively, as seen in FIGS. 4I and 4J, a plurality of tube collimators 26 may be used. Alternatively, a parallel grid collimator, for example, of 4×4, or of 16×16 cells, a wide-angle collimator, a narrow-angle collimator, or another collimator, as known, may be used.

In accordance with the present invention, probe 76 may be further adapted for focused ablation.

It will be appreciated that MRI detector 92 (FIG. 3) for nuclear-radiation imaging and MRI may be used, in place of, or in addition to ultrasound detector 32, on probe 76.

Example 3

Figure 5A:
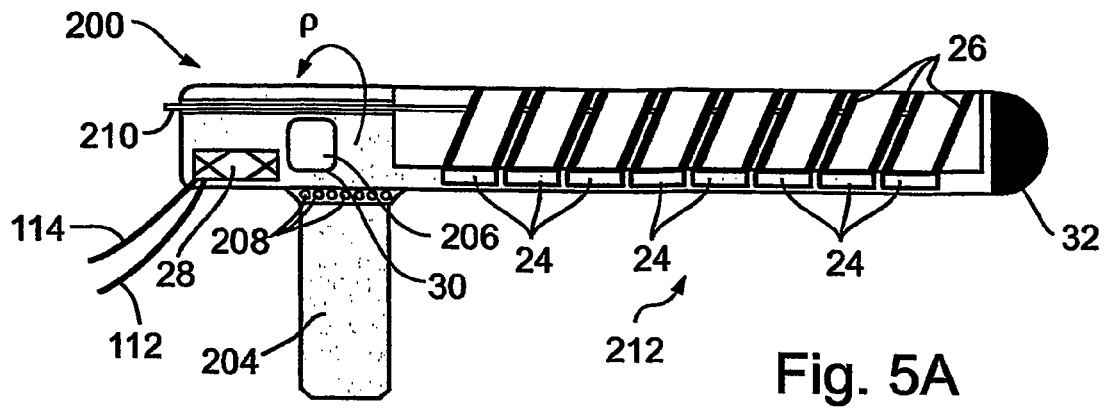
FIGS. 5A-5H schematically illustrate a rectal probe for simultaneous nuclear-radiation and ultrasound imaging, in accordance with the present invention.
Figure 5B:
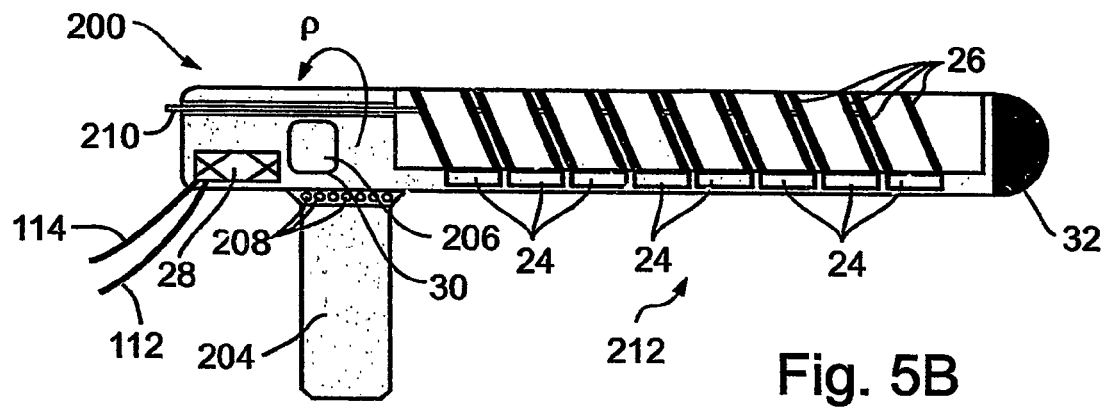
Figure 5C:
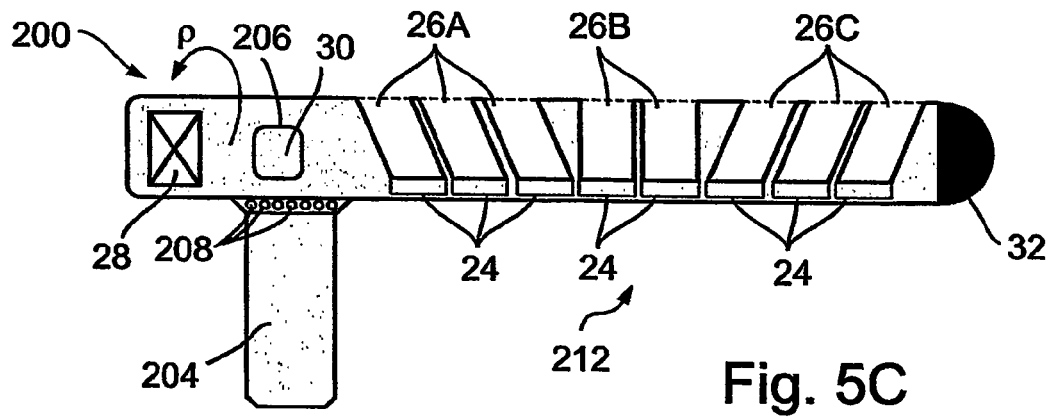
Figure 5D:
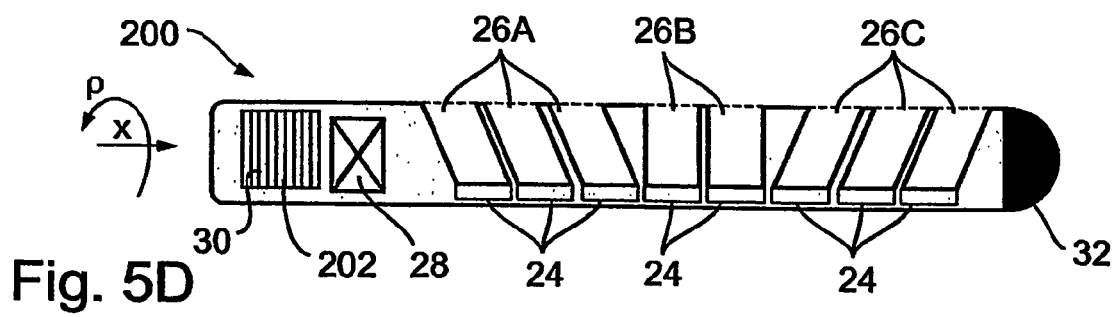
Figure 5E:
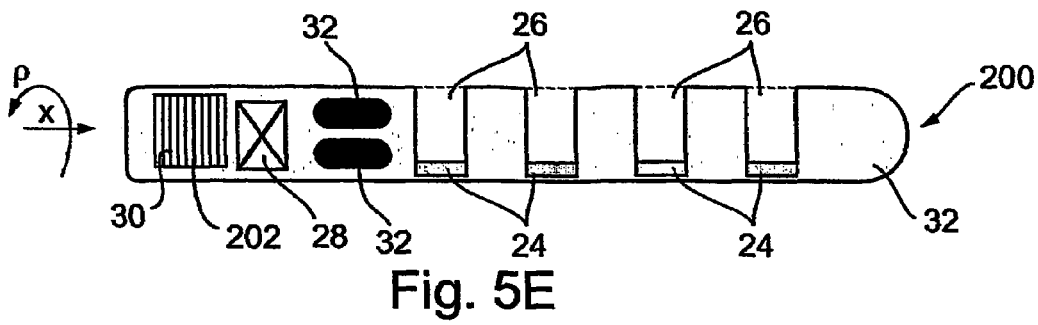

Referring further to the drawings, FIGS. 5A and 5E schematically illustrate a rectal probe 200 for simultaneous nuclear-radiation and ultrasound imaging, in accordance with the present invention, as taught in conjunction with FIG. 1A, hereinabove.

Rectal probe 200 is adapted to perform intracorporeal scanning of the rectum by nuclear radiation and ultrasound, simultaneously. Additionally, computer system 50 (FIG. 1A) is adapted to receive input from rectal probe 200 and provide an attenuation-corrected nuclear-radiation image as well as a superposition of the attenuation-corrected nuclear-radiation image and the ultrasound image, for example, on display screen 48. Furthermore, rectal probe 200 may be operative for focused ablation, for example, of a tumor, based on the superposition of the attenuation-corrected nuclear-radiation image and the ultrasound image.

As seen in FIGS. 5A-5B, rectal probe 200 includes an intracorporeal portion 112, for insertion to the rectum, and an extracorporeal portion 204, that is pressed against the body.

Intracorporeal portion 112 includes ultrasound detector 32, for example at its tip, and a plurality of nuclear radiation detectors 24, having collimators 26, which are arranged as vents and are connected to a rod 210. As rod 210 is pushed into and out of intracorporeal portion 212, collimators 26 change their orientation so as to scan in one direction (FIG. 5A), then in another (FIG. 5B).

Power and signal communication with computer system 50 (FIG. 1A) may be provided by cables 114 and 112.

Rectal probe 200 may be slowly rotated in the ρ direction, for example, against a series of roller 208 that provide a rotational interface between rotatable intracorporeal portion 212 and fixed extracorporeal portion 204.

Additionally, a motor 206 may be provided for the rotation in the ρ direction. Furthermore, motor 206 may be in communication with computer system 50, via electronic components 28 and cable 114, for reporting the exact orientation of intracorporeal portion 212. In this manner, fixed portion 204 and motor 206 together, are operative as position registering device 30 (FIG. 1A), for denoting the position of intracorporeal portion 212.

An alternative arrangement is provided in FIG. 5C, wherein collimators 26 are fixed, but are provided in three groups, 26A, 26B, and 26C, each facing a different direction.

An alternative arrangement still is provided in FIG. 5D, wherein probe 200 is intracorporeal, and includes a motor 202 for self motion in the x and ρ direction, so as to crawl into the rectum. Motor 202 may be, obtained, for example, from B-K Medical A/S, of Gentofte, DK. Additionally, motor 202 is adapted to report to computer system 50 the exact position and orientation of rectal probe 200, based on its rotation. In this manner, motor 202 is operative as position registering device 30 (FIG. 1A), for denoting the position of rectal probe 200.

Figure 5F:
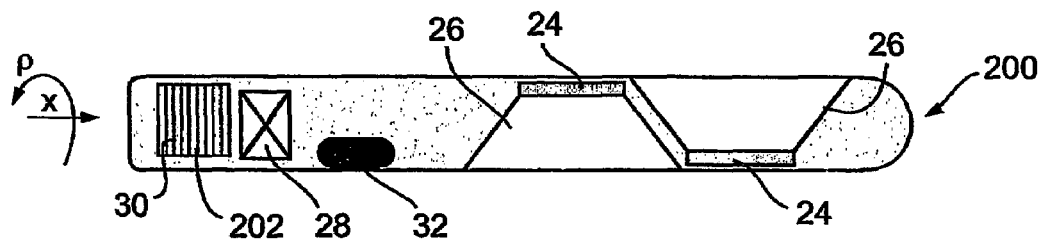
Figure 5G:
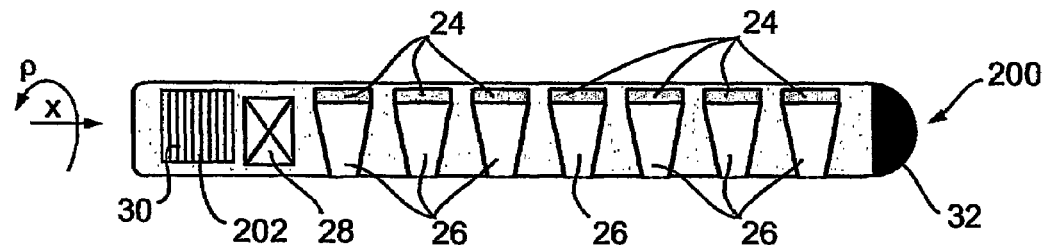
Figure 5H:
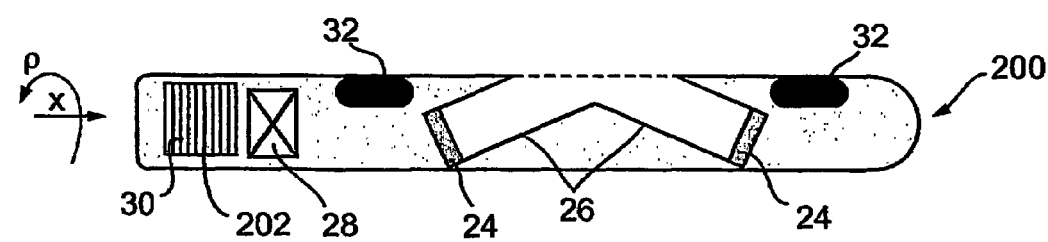

Other examples of collimators 26 and ultrasound detector arrangements 32 are provided in FIGS. 5E-5H. These include pin-hole collimators 26, for focusing at a predetermined distance (FIG. 5E), wide-angle collimators 26 (FIG. 5F), parallel collimators (FIG. 5G) and two collimators forming a wide-angle arrangement (FIG. 5H).

Ultrasound detector 32 may be at the intracorporeal tip of rectal probe 200, as seen in FIG. 5A, or along its side, as seen in FIG. 5F. Additionally, two or more ultrasound detectors 32 may be used, as seen in FIGS. 5G and 5H. The arrangement of FIGS. 5G and 5H may further be used for position registration, as taught for example, in commonly owned WO/02/058531 "Ingestible Device," whose disclosure is incorporated herein by reference. The two detectors are arranged a predetermined distance or orientation apart, in the direction of travel, and are operative to evaluate an incremental distance traveled during a period $\Delta T$, by cross correlating ultrasound echo striking ultrasound detectors 32 at a time T and at a later time $T+\Delta T$.

It will be appreciated that MRI detector 92 (FIG. 3) for nuclear-radiation imaging and MRI may be used, in place of, or in addition to ultrasound detector 32, of rectal probe 200.

Example 4

Figure 6A:
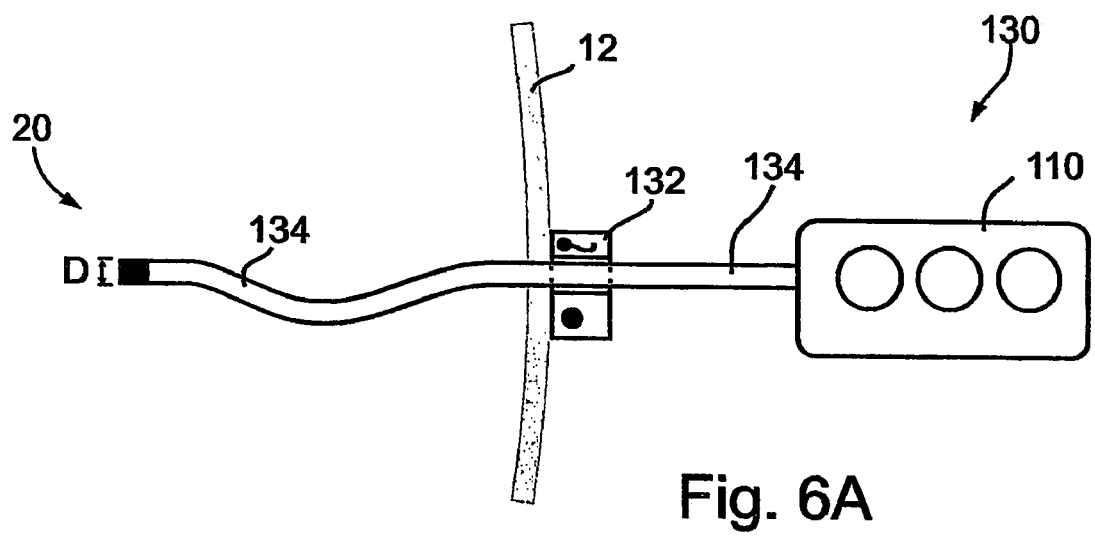
FIGS. 6A and 6B schematically illustrate an endoscopic system for simultaneous nuclear-radiation and ultrasound imaging, in accordance with the present invention.
Figure 6B:
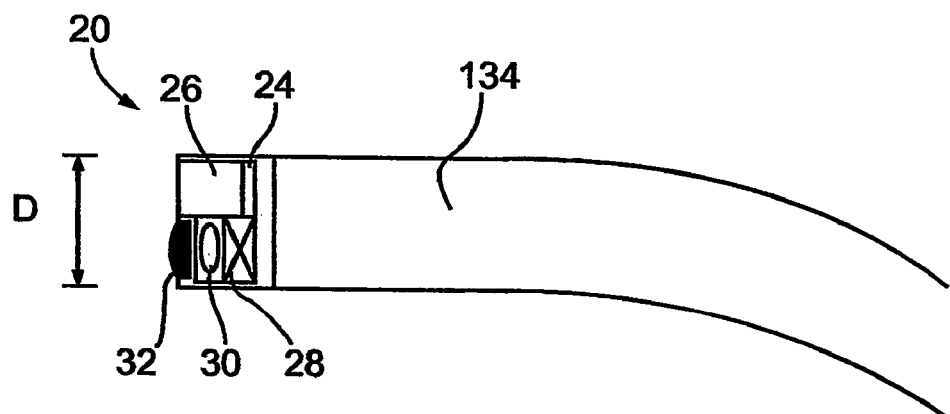

Referring further to the drawings, FIGS. 6A and 6B schematically illustrate an endoscopic system 130 for simultaneous nuclear-radiation and ultrasound imaging, in accordance with the present invention, as taught in conjunction with FIG. 1A, hereinabove.

Endoscopic system 130 may be adapted for insertion through a trucar valve 132, through tissue 12, during minimally invasive surgery. Thus a diameter D of endoscopic probe 20 is generally no greater than 12 mm.

Furthermore, computer system 50 (FIG. 1A) is adapted to receive input from endoscopic system 130 and provide an attenuation-corrected nuclear-radiation image as well as a superposition of the attenuation-corrected nuclear-radiation image and the ultrasound image, for example, on display screen 48.

Preferably, endoscopic system 130 is mounted on a shaft 134 and includes combined nuclear-radiation and ultrasound imaging probe 20, having nuclear-radiation detector 24, preferably also, collimator 26, ultrasound detector 32, and preferably six-dimensional, position-registering device 30.

Endoscopic system 130 further includes control unit 110, which remains extracorporeal, for activating and deactivating endoscopic system 130. Control unit 110 may include basic control knobs, such as "stop", "start", and "pause." Preferably, control unit 110 is adapted to operate nuclear-radiation imaging, alone, ultrasound imaging, alone, and nuclear-radiation and ultrasound imaging, simultaneously.

In accordance with the present invention, ultrasound detector 32 is further adapted for focused ablation.

It will be appreciated that combined probe 91 (FIG. 3) for nuclear-radiation imaging and MRI may be used, in place of probe 20, as taught in conjunction with FIG. 3.

It will be appreciated that separate probes for nuclear radiation and ultrasound, or for nuclear radiation and magnetic resonance may similarly be used, as taught in conjunction with FIG. 2A or 2B.

Example 5

Figure 7A:
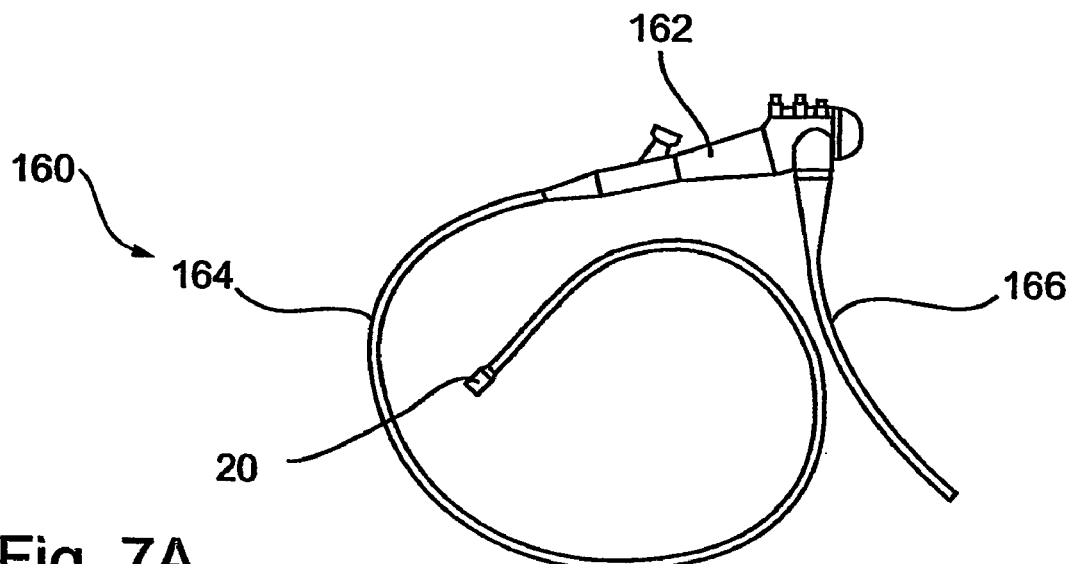
FIGS. 7A and 7B schematically illustrate an endoscopic system for simultaneous nuclear-radiation and ultrasound imaging, in accordance with the present invention.
Figure 7B:
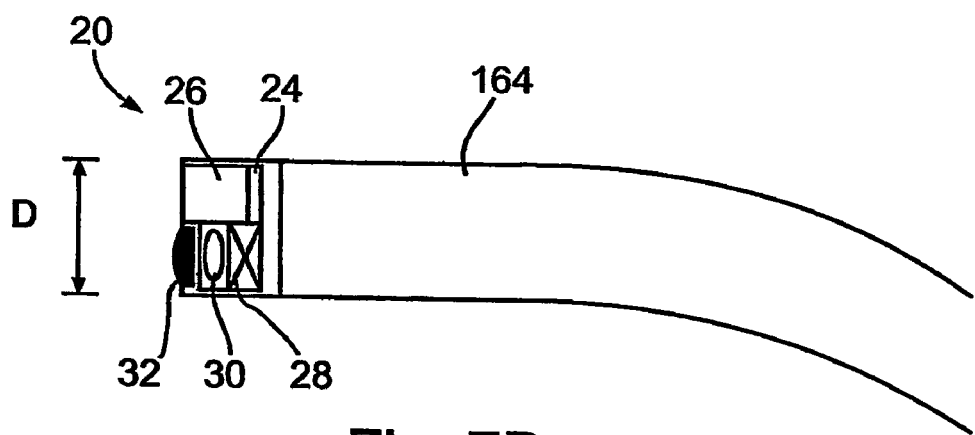

Referring further to the drawings, FIGS. 7A and 7B schematically illustrate an endoscopic system 160 for simultaneous nuclear-radiation and ultrasound imaging, in accordance with the present invention, as taught in conjunction with FIG. 1A, hereinabove.

Endoscopic system 160 may be adapted for insertion through a body lumen, for example, through the digestive tract. Endoscopic system 160 includes a flexible shaft 164, an extracorporeal control system 162, and a signal and power cable 166. Combined probe 20 may be positioned at the tip of flexible shaft 164.

The operation of endoscopic system 160 is similar to that of endoscopic system 130, hereinabove.

In accordance with the present invention, ultrasound detector 32 is further adapted for focused ablation.

It will be appreciated that combined probe 91 (FIG. 3) for nuclear-radiation imaging and MRI may be used, in place of probe 20, as taught in conjunction with FIG. 3.

It will be appreciated that separate probes for nuclear radiation and ultrasound, or for nuclear radiation and magnetic resonance may similarly be used, as taught in conjunction with FIG. 2A or 2B.

Example 6

Figure 8A:
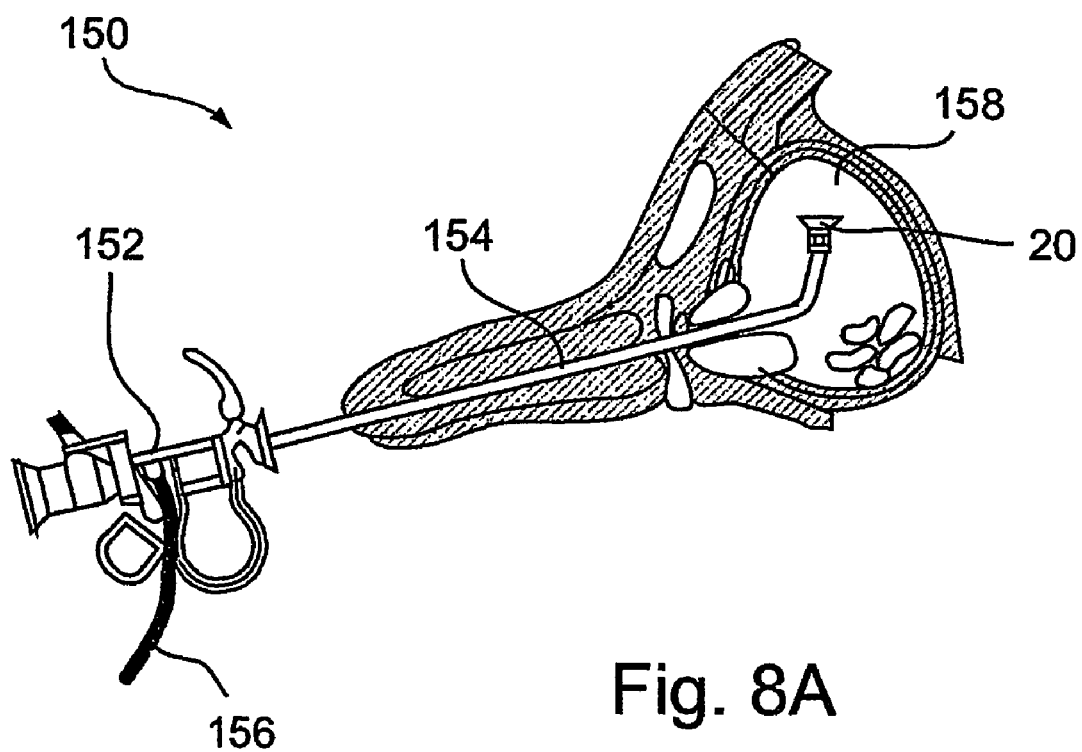
FIGS. 8A and 8B schematically illustrate an endoscopic system for simultaneous nuclear-radiation and ultrasound imaging, in accordance with the present invention.
Figure 8B:
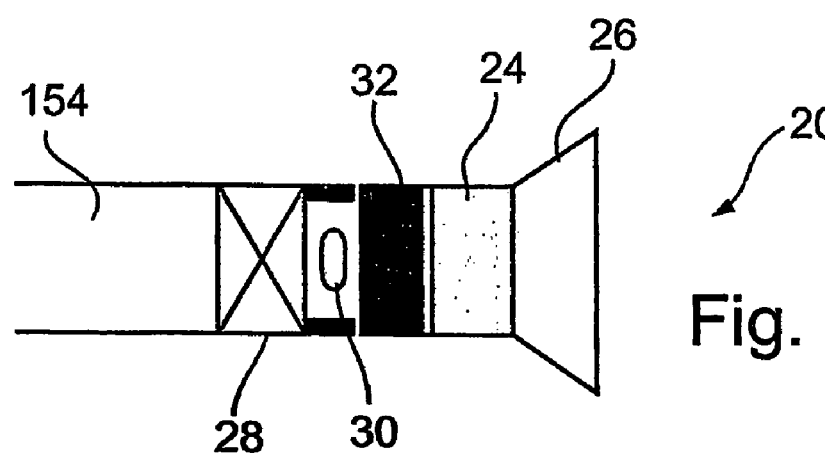

Referring further to the drawings, FIGS. 8A and 8B schematically illustrate an endoscopic system 150 for simultaneous nuclear-radiation and ultrasound imaging, in accordance with the present invention, as taught in conjunction with FIG. 1A, hereinabove.

Endoscopic system 150 is similar to a resectoscope, and includes a flexible shaft 154, an extracorporeal control system 152, and a signal and power cable 156, and is adapted for insertion through a urinary tract, for imaging of a bladder 158.

Combined probe 20 may be positioned at the tip of flexible shaft 154.

The operation of endoscopic system 150 is similar to that of endoscopic system 130, hereinabove.

In accordance with the present invention, ultrasound detector 32 is further adapted for focused ablation.

It will be appreciated that combined probe 91 (FIG. 3) for nuclear-radiation imaging and MRI may be used, in place of probe 20, as taught in conjunction with FIG. 3.

It will be appreciated that separate probes for nuclear radiation and ultrasound, or for nuclear radiation and magnetic resonance may similarly be used, as taught in conjunction with FIG. 2A or 2B.

Example 7

Referring further to the drawings, FIGS. 9A and 9B schematically illustrate ingestible devices 170 for simultaneous nuclear-radiation and ultrasound imaging, in accordance with the present invention, as taught in conjunction with FIG. 1A, hereinabove.

As seen in FIG. 9A, ingestible device 170 is adapted to travel through the digestive tract and perform imaging thereto, as taught in commonly owned WO/02/058531 "Ingestible Device," whose disclosure is incorporated herein by reference.

Ingestible device 170 may include a plurality of nuclear radiation detectors 24, associated collimators 26, at least one, and preferably two or more ultrasound detectors 32, and related electronics 28. A very thin polymeric material, which is substantially transparent to nuclear radiation, forms a skin 175 to ingestible device 170.

Additionally, ingestible device 170 includes a controller 172, which may be any one of a dedicated control circuitry, a processor, an ASIC, or a microcomputer, as known, and may further include a memory unit, integrated with it, a battery 174, a transceiver 176, and position registering device 30. It will be appreciated that separate transmitter and receiver may be used.

It will be further appreciated that both nuclear radiation detectors 24 and ultrasound detectors 32 may be operative also as position registering device, evaluating an incremental distance traveled during a period ΔT, by cross correlating ultrasound echo striking ultrasound detectors 32 at a time T and at a later time T+ΔT. Alternatively nuclear radiation detectors 24 may be used for cross correlating nuclear radiation striking nuclear-radiation detectors 24 at a time T and at a later time T+ΔT.

Ingestible device 170 is thus operable as combined probes 20, for scanning by nuclear radiation and ultrasound, simultaneously. Additionally, computer system 50 (FIG. 1A) is adapted to receive input from ingestible device 20, in a wireless manner, and provide an attenuation-corrected nuclear-radiation image as well as a superposition of the attenuation-corrected nuclear-radiation image and the ultrasound image, for example, on display screen 48.

Alternatively, as seen in FIG. 9B, ingestible device 170 has no collimators.

It will be appreciated that MRI detector 92 (FIG. 3) for nuclear-radiation imaging and MRI may be used, in place of, or in addition to ultrasound detectors 32.

Example 8

Referring further to the drawings, FIGS. 10A and 10B schematically illustrate a three-dimensional system 180, for simultaneous nuclear-radiation and ultrasound imaging, in accordance with the present invention, as taught in conjunction with FIG. 2B, hereinabove.

System 180 is analogous to system 80 of FIG. 2B. Thus, two separate gantries may be used, for nuclear radiation imaging for example, SPECT, PET and for three-dimensional ultrasound imaging. Each modality is performed, individually, and computer system 50 combines the results.

Thus, Computer system 50 (FIG. 2B) receives input from system 180 and provide an attenuation-corrected, three-dimensional nuclear-radiation image as well as a superposition of the three-dimensional attenuation-corrected nuclear-radiation image and the three-dimensional ultrasound image, for example, on display screen 48. Furthermore, system 180 may be operative to guide in-vivo instrument tip 25 (FIG. 1H) based on the superposition of the attenuation-corrected nuclear-radiation image and the ultrasound image, for example, as seen on display screen 48 (FIG. 1H).

Alternatively, system 82 may be a CT.

Additionally, or alternatively, system 86 may be an MRI.

Example 9

Figure 11A:
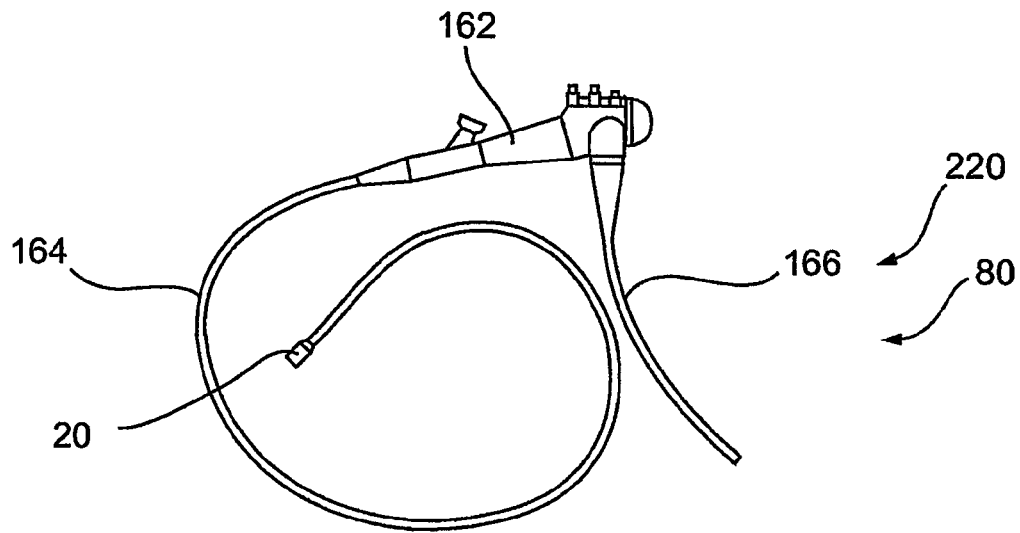
FIGS. 11A-11C schematically illustrate a system, which includes an intracorporeal, nuclear-radiation endoscopic probe and an extracorporeal, handheld ultrasound probe, for simultaneous nuclear-radiation and ultrasound imaging, in accordance with the present invention.
Figure 11B:
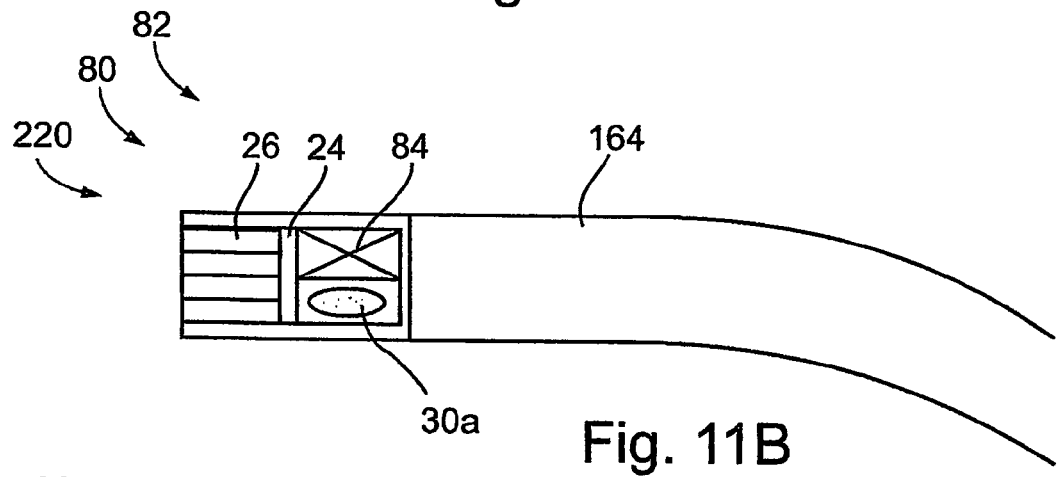
Figure 11C:
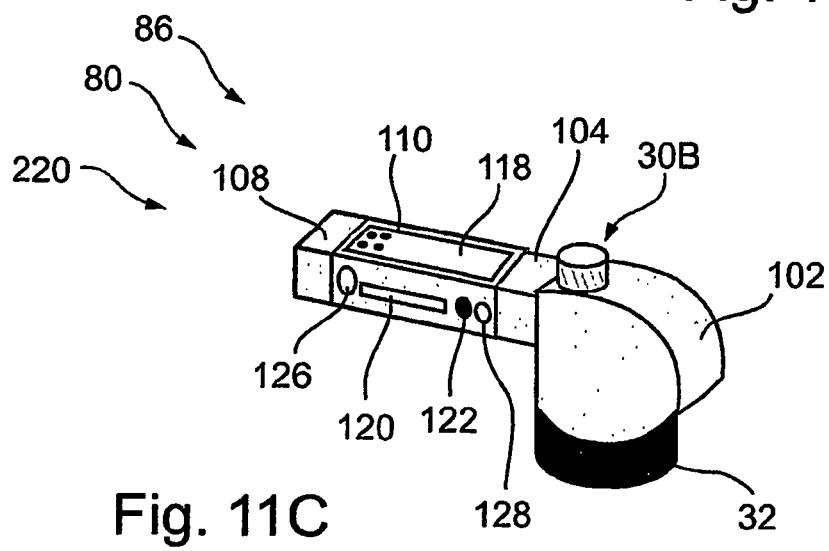

Referring further to the drawings, FIGS. 11A-11C schematically illustrate a system 220, which is analogous to system 80 of FIG. 2B hereinabove, and includes intracorporeal, nuclear-radiation endoscopic probe 82 and extracorporeal, handheld ultrasound probe 86, for simultaneous nuclear-radiation and ultrasound imaging, in accordance with the present invention.

The two modality may be performed together, for example, by two operators, or one after the other. Computer system 150 combines the results.

In this manner, ultrasound attenuation correction may be performed even when the endoscopic probe is very small and contains only a single detector.

It will be appreciated that a three-dimensional ultrasound or MRI may be used in place of the extracorporeal, handheld probe.

Example 10

As taught in commonly owned, U.S. patent application Ser. No. 10/686,536 to Kimchy et al., entitled, "Blood Vessels Wall Imaging Catheter," filed on Oct. 16, 2003, nuclear-radiation detector 24 may be a scintillation optical fiber, for example, for intravascular imaging. The location of a radiation event along the optical fiber may be determined by algorithms that differentiate between the times that a single event reaches both ends of the fiber. For example, when the event occurs exactly along the middle of the fiber, it will be sensed by the two ends, simultaneously. In general, the scintillation optical fiber is inserted through a catheter.

Intravascular coronary ultrasound (IVUS) is also a catheter-based procedure, in which a tiny ultrasound camera is inserted into a coronary arteries for example, for detecting locations of plaque. A position registration device may be included with the ultrasound camera.

In accordance with the present invention, intravascular nuclear-radiation imaging and intravascular ultrasound imaging may be performed as a single catheter-based procedure, performed in series, using the same catheter, for obtaining radiation attenuation correction by ultrasound, for the nuclear-radiaiton image, and for superposition of the two images.

Figure 12A:
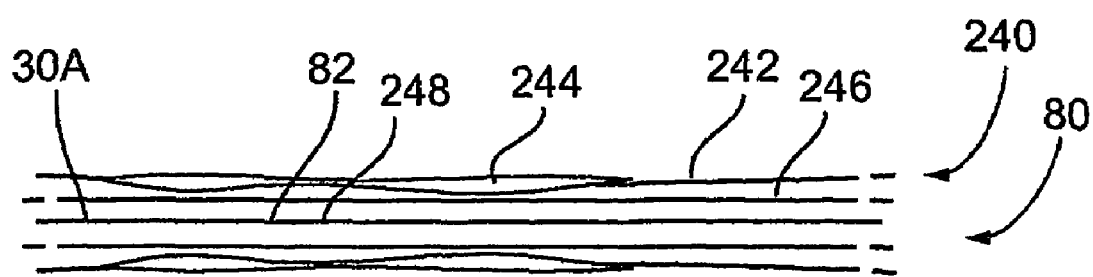
FIGS. 12A and 12B schematically illustrate an intraavascular system, for simultaneous nuclear-radiation and ultrasound imaging, in accordance with the present invention.
Figure 12B:
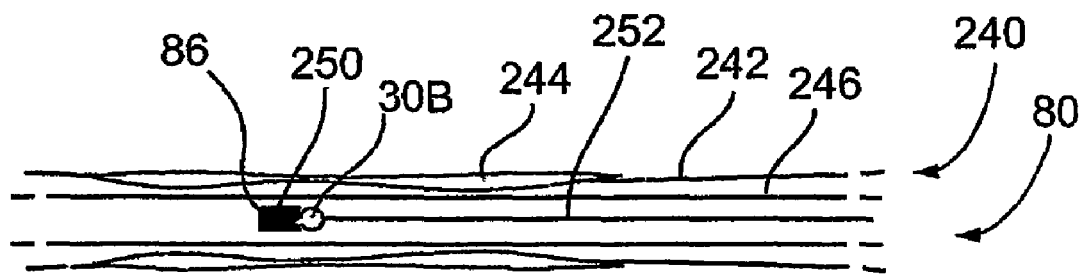

Referring further to the drawings, FIGS. 12A-12B schematically illustrate a system 240, which is analogous to system 80 of FIG. 2B hereinabove, and includes intravascular, nuclear-radiation detector 82, formed as a scintillation optical fiber, and intravascular ultrasound camera 86, for nuclear-radiation and ultrasound imaging, in accordance with the present invention.

FIGS. 12A-12B show a blood vessel 242, which includes some plaque 244, and to which a catheter 246 has been inserted.

In FIG. 12A, an optical fiber 248 is inserted into catheter 246. It is operative as probe 82 of system 80 (FIG. 2B), but also as position registering device 30A therein.

In FIG. 12B an IVUS camera 250 is inserted into catheter 246, via a guide wire 252. Preferably, it includes position registration device 30B. IVUS camera is operative as probe 86 of system 80. (FIG. 2B).

The two modality may be performed one after the other. Computer system 50 combines the results.

Example 11

In accordance with the present invention, combined probe 20 or combine probe 91 may further include a detachable needle guide, for collecting tissue samples, as taught by U.S. Pat. No. 6,443,902 to Sasady, dated Sep. 3, 2002, and entitled, Ultrasound probe with a detachable needle guide, for collecting tissue samples," whose disclosure is incorporated herein by reference.

Example 12

In accordance with the present invention, ultrasound detector 32 may be constructed in accordance with the teaching of U.S. Pat. No. 6,293,912, dated Sep. 25, 2001, and entitled, "Ultrasound scanner with beam former," whose disclosure is incorporated herein by reference, wherein the ultrasound has an emitting transducer and a receiving transducer with a plurality of transducer elements. Electrical signals from the receiving transducer elements are selectively connected to input taps of a single delay line for individually delaying the electrical signals to compensate for their different distances from points under investigation in the object. For each point in the object a first received echo signal is connected to a first input tap giving a first delay, and subsequently received echo signals are connected to input taps being selected so that the subsequent electrical signals are output on the output tap substantially simultaneously with the electrical signal representing the first received echo. The receiving transducer is thereby adjusted currently during the reception of each scan line to perfectly adapt its focus at each instant in time and with an exceptionally high degree of accuracy. Additionally, switching noise in the switching network at the input of the delay line is canceled by first recording a scan line without signal from the emitting transducer as reference signals and subtracting these scan line reference signals from subsequent ultrasound echo signals.

As used herein the term "about" refers to ±10%.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Imaging apparatus, comprising:
   a first device which obtains a first image, by a first modality, said image being an ionizing radiation image, wherein said first image is registered to a system of coordinates;

a second device which obtains a second, structural image, by a second modality, said structural image being an ultrasonic image; and a computerized system, which comprises:
- a registrator for co-registering said second, structural image to said system of coordinates, and
- an attenuation-instruction generator configured to compute a set of attenuation instructions for said first image, based at least on non-uniformities in said second, structural image.

2. The imaging apparatus of claim 1, wherein said computerized system is further configured to compute, based on said a set of attenuation instructions an attenuation-corrected image of said first image.

3. The imaging apparatus of claim 2, wherein said computerized system is further configured to display a superposition of said attenuation-corrected first image and said second, structural image.

4. The imaging apparatus of claim 3, wherein said apparatus further includes an instrument, registered to said system of coordinates and visible on at least one of said first image and said second, structural image, and wherein said computerized system is further configured to guide said instrument in-vivo, based on said superposition.

5. The imaging apparatus of claim 1, wherein said registrator for co-registering said second, structural image to said system of coordinates relies on that said first and second devices share a single position-registration device, for co-registering said second, structural image to said system of coordinates.

6. The imaging apparatus of claim 1, wherein said registrator for co-registering said second, structural image to said system of coordinates relies on that said first and second devices have substantially equal position-registration devices, for co-registering said second, structural image to said system of coordinates.

7. The imaging apparatus of claim 1, wherein said registrator for co-registering said second, structural image to said system of coordinates relies on fiduciary marks visible both on said first image and on said second, structural image, for co-registering said second, structural image to said system of coordinates.

8. The imaging apparatus of claim 1, further comprising an ultrasound transducer operative for focused ablation.

9. The imaging apparatus of claim 1, designed as a rectum probe.

10. The imaging apparatus of claim 1, designed as an endoscope probe.

11. The imaging apparatus of claim 1, designed to be inserted through a trucar valve.

12. The imaging apparatus of claim 1, designed to be mounted on a resectoscope.

13. The imaging apparatus of claim 1, designed to be inserted in a catheter.

14. The imaging apparatus of claim 1, designed for intravascular imaging.

15. The imaging apparatus of claim 1, designed as a hand-held, extracorporeal probe.

16. An imaging apparatus according to claim 1, arranged as an intrabody probe, comprising
an intracorporeal portion, which portion comprises said first device and said second device.

17. The imaging apparatus of claim 16, further comprising movable collimators, operative as vents.

18. The imaging apparatus of claim 16, comprising a motor which further includes motion and position registration in a linear direction into the rectum.

19. The imaging apparatus of claim 16, further comprising an ultrasound transducer, adapted for focused ablation.

20. Imaging apparatus according to claim 1, wherein said first modality is selected from a group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof.

21. Imaging apparatus according to claim 1, wherein said first modality is selected from the group consisting of a gamma scan, a beta scan, and a combination thereof.

22. Imaging apparatus according to claim 1, wherein said generator generates said attenuation instructions based on an identification of boundaries between tissues in said structural image.

23. Imaging apparatus according to claim 1, wherein said generator generates said attenuation instructions based on a characterization of tissues in said image according to tissue types.

24. Imaging apparatus according to claim 1, wherein said generator generates said attenuation instructions based on a 3D structural image.

25. Imaging apparatus according to claim 1, wherein said first device and said second device are mounted on an elongate element and occupy different axial locations.

26. An imaging method, comprising:
- imaging by a first modality, a first image, by ionizing radiation;
- imaging by a second modality, a second, structural image, said structural image being an ultrasonic image; and
- computing a set of attenuation instructions for said first image, based at least on non-uniformities in said second, structural image.

27. The imaging method of claim 26, further comprising, based on said a set of attenuation instructions, computing an attenuation-corrected first image.

28. The imaging method of claim 27, further comprising displaying said attenuation-corrected first image.

29. The imaging method of claim 27, further comprising superimposing said attenuation-corrected first image and a second, structural image of said second, structural imaging modality.

30. The imaging method of claim 29, further comprising guiding an instrument based on the superposition of said attenuation-corrected first image and said second, structural image.

31. The imaging method of claim 29, further comprising performing focused ablation, based on the superposition of said attenuation-corrected first image and said second, structural image.

32. A method according to claim 26, wherein said first modality is selected from a group consisting of SPECT, PET, CT, an extracorporeal gamma scan, an extracorporeal beta scan, x-rays, an intracorporeal gamma scan, an intracorporeal beta scan, an intravascular gamma scan, an intravascular beta scan, and a combination thereof.

* * * * *

UNITED STATES PATENT AND TRADEMARK OFFICE
CERTIFICATE OF CORRECTION

PATENT NO. : 7,652,259 B2 Page 1 of 1
APPLICATION NO. : 10/533568
DATED : January 26, 2010
INVENTOR(S) : Yoav Kimchy et al.

It is certified that error appears in the above-identified patent and that said Letters Patent is hereby corrected as shown below:

Priority Data:
On the Title Page, insert in the section marked

Item [60]   Related U.S. Application Data

--US Application No. 10/616,307 filed on July 10, 2003

US Application No. 10/616,301 filed on July 10, 2003--

Signed and Sealed this

Twenty-seventh Day of April, 2010

David J. Kappos
*Director of the United States Patent and Trademark Office*